US012351609B2

(12) United States Patent
Olson et al.

(10) Patent No.: US 12,351,609 B2
(45) Date of Patent: *Jul. 8, 2025

(54) USE OF A SMALL NATIVE PEPTIDE ACTIVATOR OF SERCA PUMP FOR TREATMENT OF HEART FAILURE AND OTHER DISORDERS CHARACTERIZED BY CYTOSOLIC CALCIUM OVERLOAD

(71) Applicant: The Board of Regents of the University of Texas System, Austin, TX (US)

(72) Inventors: Eric N. Olson, University Park, TX (US); Rhonda S. Bassel-Duby, Dallas, TX (US); Catherine A. Makarewich, Dallas, TX (US); Benjamin R. Nelson, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/392,137

(22) Filed: Aug. 2, 2021

(65) Prior Publication Data

US 2021/0380650 A1 Dec. 9, 2021

Related U.S. Application Data

(60) Continuation of application No. 16/743,831, filed on Jan. 15, 2020, now Pat. No. 11,111,278, which is a division of application No. 15/491,057, filed on Apr. 19, 2017, now Pat. No. 10,570,183.

(60) Provisional application No. 62/324,706, filed on Apr. 19, 2016.

(51) Int. Cl.
*C07K 14/47* (2006.01)
*A61K 38/17* (2006.01)
*A61K 45/06* (2006.01)
*A61K 48/00* (2006.01)

(52) U.S. Cl.
CPC .......... *C07K 14/47* (2013.01); *A61K 38/1709* (2013.01); *A61K 45/06* (2013.01); *A61K 48/0058* (2013.01)

(58) Field of Classification Search
CPC ................ A61K 38/1709; A61K 45/06; A61K 48/0058; C07K 14/47
See application file for complete search history.

(56) References Cited

U.S. PATENT DOCUMENTS

| | | |
|---|---|---|
| 6,822,072 B1 | 11/2004 | Edwards et al. |
| 7,235,381 B2 | 6/2007 | Edwards et al. |
| 2003/0175795 A1 | 9/2003 | Walker et al. |
| 2012/0252882 A1 | 10/2012 | Chuah et al. |

OTHER PUBLICATIONS

"A small protein plays a big role in heart muscle contraction," *Science Daily*, located at https://www.sciencedaily.com/releases/2016/01/160114212441.htm, published Jan. 16, 2016.
Bi et al., "Control of muscle formation by the fusogenic micropeptide myomixer," *Science*, 356(6335):323-327, 2017.
Expasy Translate Tool, accessed on Jan. 18, 2018, Swiss Institute of Bioinformatics.
Micheletti et al, "Istaroxime, a stimulator of sarcoplasmic reticulum calcium adenosine triphosphate isoform 2a activity, as a novel therapeutic approach to heart failure," *American Journal of Cardiology*, 99[suppl]:24A-32A, 2007.
Nelson et al., "A peptide encoded by a transcript annotated as long noncoding RNA enhances SERCA activity in muscle," *Science*, 351(6270):271-5, 2016.
Office Action issued in U.S. Appl. No. 15/491,057, mailed Aug. 31, 2017.
Office Action issued in U.S. Appl. No. 15/491,057, mailed Apr. 12, 2019.
Office Action issued in U.S. Appl. No. 15/491,057, mailed Feb. 22, 2018.
Office Action issued in U.S. Appl. No. 15/491,057, mailed Sep. 21, 2018.
Office Action issued in U.S. Appl. No. 16/743,831, mailed Jul. 21, 2020.
Office Action issued in U.S. Appl. No. 16/743,831, mailed Dec. 10, 2020.
Olson, "New Insights into Muscle Development, Disease and Regeneration," located at https://professional.heart.org/idc/groups/ahamah-public/@wcm/@sop/@scon/documents/downloadable/ucm_475703.pdf, retrieved Oct. 4, 2017.

*Primary Examiner* — Lianko G Garyu
*Assistant Examiner* — Erinne R Dabkowski
(74) *Attorney, Agent, or Firm* — Parker Highlander PLLC

(57) ABSTRACT

The present disclosure describes a new native peptide designated herein as Dwarf Open Reading Frame, or DWORF. This peptide enhances the apparent activity of the SERCA pump, is positively inotropic and lusitropic, and therefore is provided as a therapeutic agent for disorders characterized by cytosolic calcium overload.

20 Claims, 14 Drawing Sheets

Specification includes a Sequence Listing.

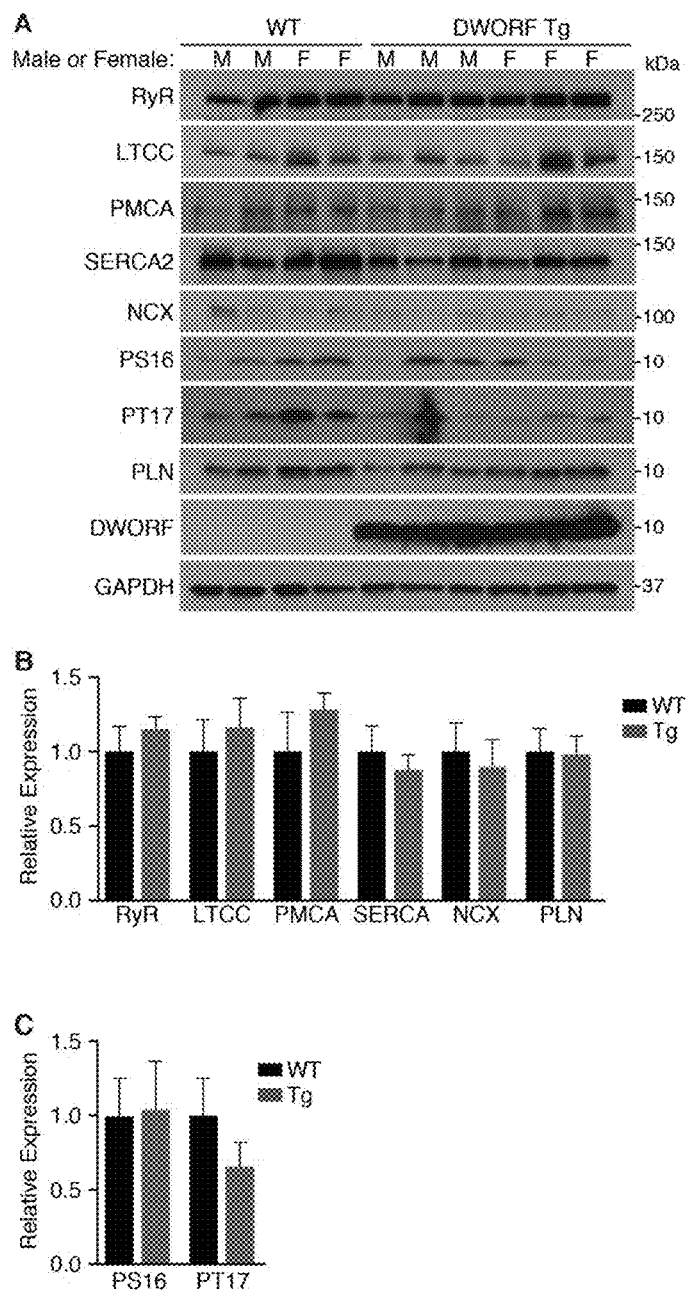
FIGS. 8A-C

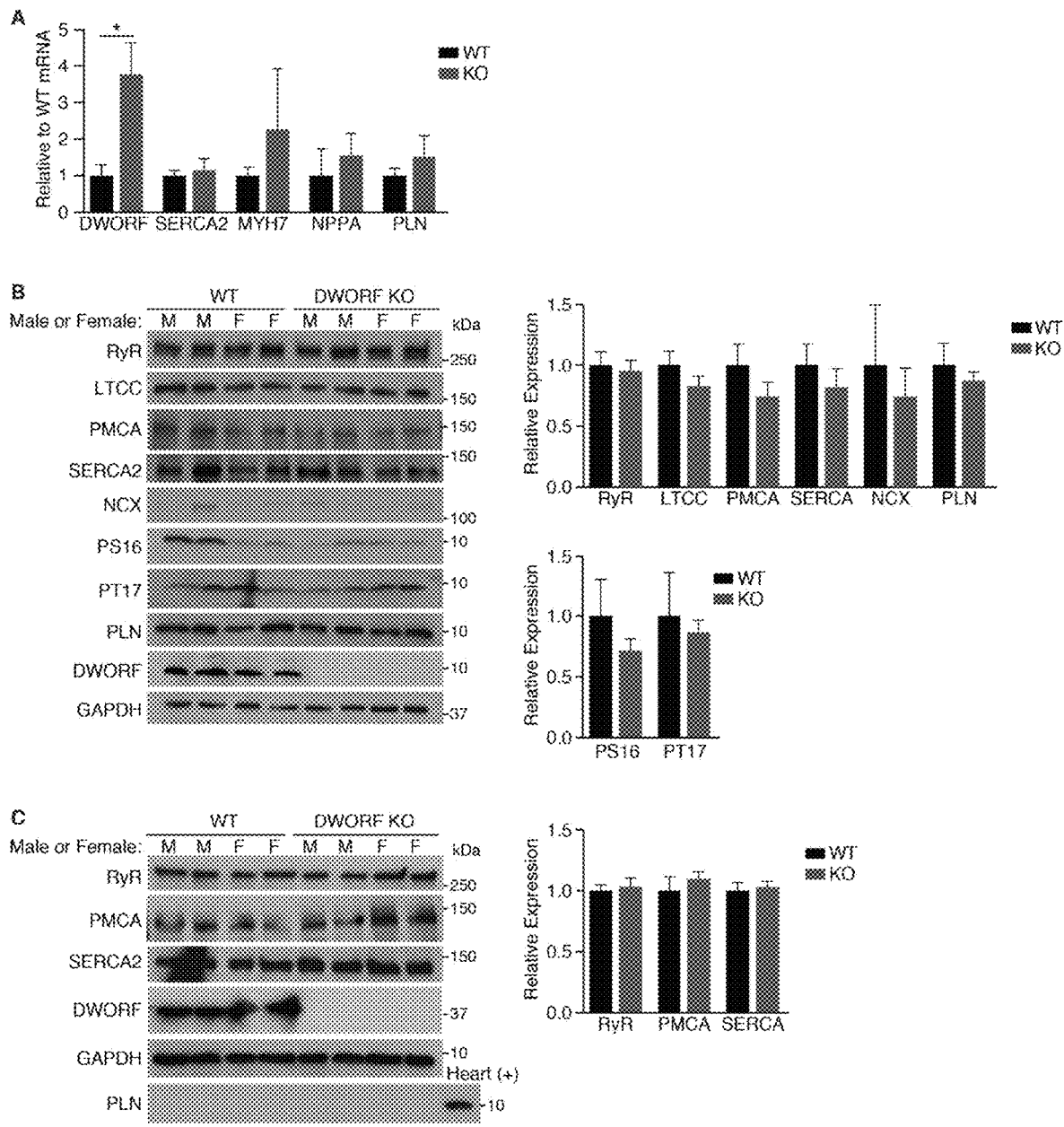
FIGS. 9A-C

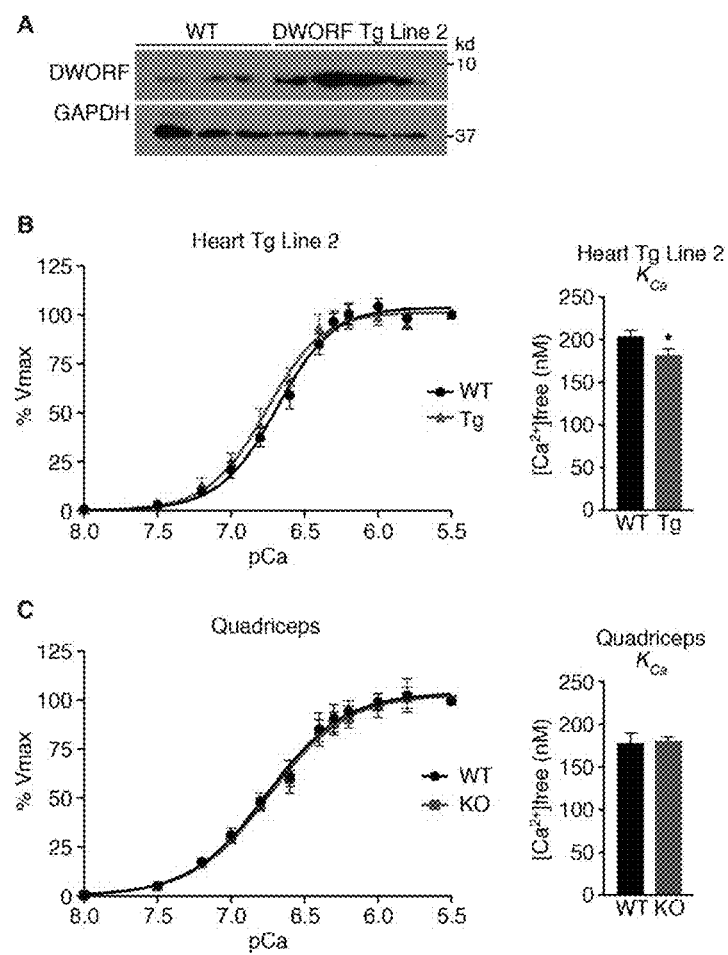
FIGS. 10A-C

```
DWORF 34M  MAEK-ESTSPHLMVPILLLVGWIVGCIIVIYIVFF(SEQ ID NO: 1)
DWORF 35M  MAEKAESTSPHLMVPILLLVGWIVGCIIVIYIVFF(SEQ ID NO: 5)
DWORF 34I  MAEK-ESTSPHLIVPILLLVGWIVGCIIVIYIVFF(SEQ ID NO: 7)
DWORF 35I  MAEKAESTSPHLIVPILLLVGWIVGCIIVIYIVFF(SEQ ID NO: 9)
```

Splice variant(bold); SNP (underline)

FIG. 11A

DWORF 34M

ATGGCTGAGAAAGAGTCAACATCACCACACCTCATGGTTCCCATTCTTCTCCTGGTTGG
ATGGATTGTAGGCTGCATCATCGTTATTTACATTGTCTTCTTCTAA
(SEQ ID NO: 2)

DWORF 35M

ATGGCTGAGAAAGCAGAGTCAACATCACCACACCTCATGGTTCCCATTCTTCTCCTGGT
TGGATGGATTGTAGGCTGCATCATCGTTATTTACATTGTCTTCTTCTAA
(SEQ ID NO: 6)

DWORF 34I

ATGGCTGAGAAAGAGTCAACATCACCACACCTCATTGTTCCCATTCTTCTCCTGGTTGG
ATGGATTGTAGGCTGCATCATCGTTATTTACATTGTCTTCTTCTAA
(SEQ ID NO: 8)

DWORF 35I

ATGGCTGAGAAAGCAGAGTCAACATCACCACACCTCATTGTTCCCATTCTTCTCCTGGT
TGGATGGATTGTAGGCTGCATCATCGTTATTTACATTGTCTTCTTCTAA
(SEQ ID NO: 10)

FIG. 11B

Human DWORF Protein Sequence

MAEKAGSTFSHLLVPILLLIGWIVGCIIMIYVVFS* (SEQ ID NO: 3)

Human DWORF DNA Sequence atggctgaaaaagcggggtctacattttcacaccttctggttcctattcttctcctgattggctggattgtgggctgcatcataatgatt
tatgttgtcttctcttag (SEQ ID NO: 4)

FIG. 12

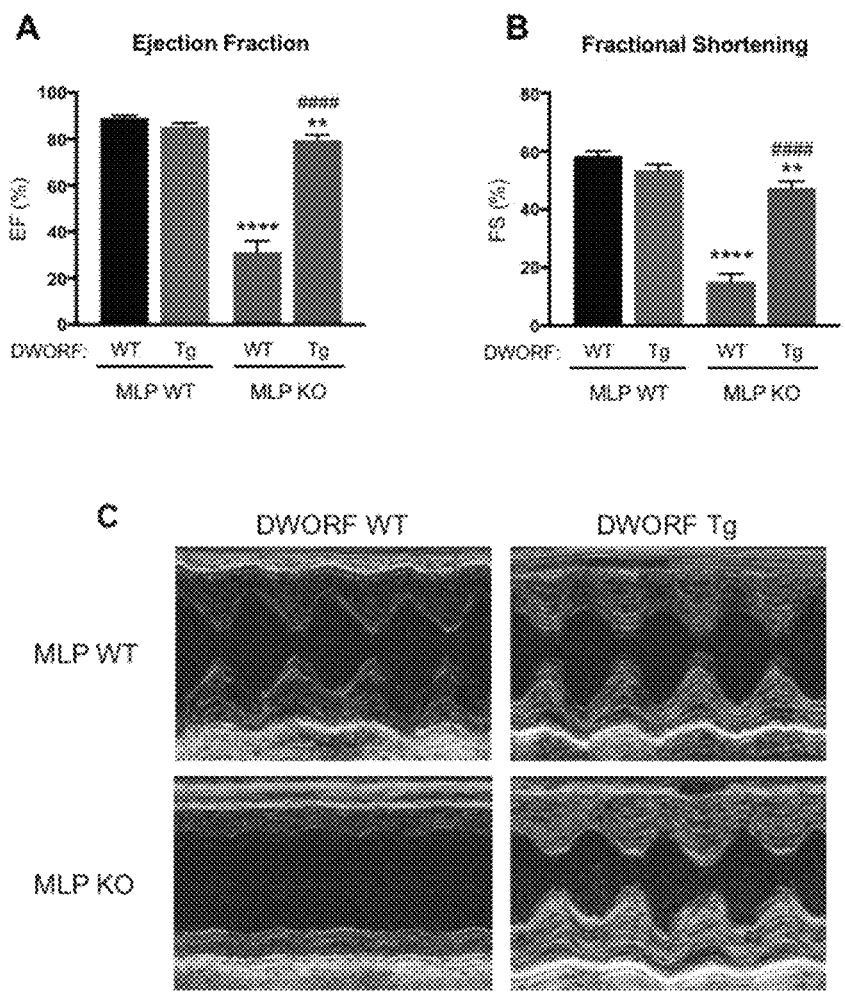
FIGS. 13A-C

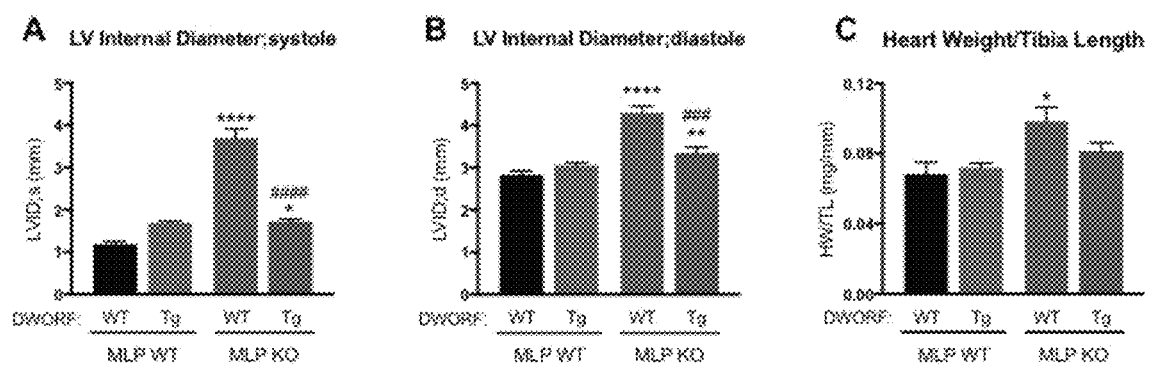
FIGS. 14A-C

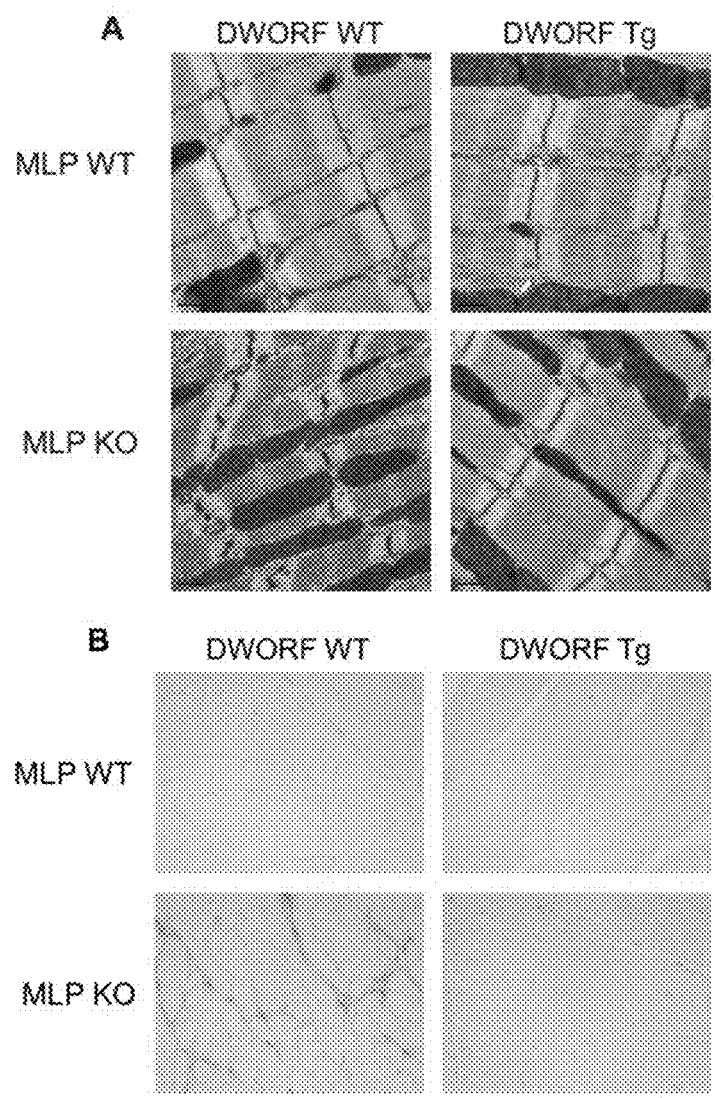
FIGS. 15A-B

USE OF A SMALL NATIVE PEPTIDE ACTIVATOR OF SERCA PUMP FOR TREATMENT OF HEART FAILURE AND OTHER DISORDERS CHARACTERIZED BY CYTOSOLIC CALCIUM OVERLOAD

This application is a continuation of U.S. application Ser. No. 16/743,831, filed Jan. 15, 2020, which is a divisional of U.S. application Ser. No. 15/491,057, filed Apr. 19, 2017, now U.S. Pat. No. 10,570,183, which claims benefit of priority to U.S. Provisional Application Ser. No. 62/324,706, filed Apr. 19, 2016, the entire contents of each of which are hereby incorporated by reference.

FEDERAL SUPPORT CLAUSE

This invention was made with government support under grant nos. R01 HL077439-10 and R01 DK099653-01 awarded by National Institutes of Health. The government has certain rights in the invention.

INCORPORATION OF SEQUENCE LISTING

The sequence listing that is contained in the file named "UTSDP2982USC1.txt", which is 11 KB (as measured in Microsoft Windows®) and was created on Aug. 1, 2021, is filed herewith by electronic submission and is incorporated by reference herein.

BACKGROUND

1. Field

The present disclosure relates generally to the fields of molecular biology, cell physiology and medicine. More particularly, it concerns the identification of a native small peptide that enhances the activity of the sarco/endoplasmic reticulum calcium ATPase, also known as SERCA.

2. Description of Related Art

Intracellular $Ca^{2+}$ cycling is vitally important to the function of striated muscles and is altered in many muscle diseases. Upon electrical stimulation of the myocyte plasma membrane, $Ca^{2+}$ is released from the sarcoplasmic reticulum (SR) and binds to the contractile apparatus triggering muscle contraction (Bers, 2002). Relaxation occurs when $Ca^{2+}$ is pumped back into the sarcoplasmic reticulem (SR) by the sarco/endoplasmic reticulum $Ca^{2+}$ ATPase (SERCA). SERCA activity is inhibited by the small transmembrane peptides phospholamban (PLN), sarcolipin (SLN), and myoregulin (MLN) in vertebrates and by sarcolamban A and B (sclA and sclB) in invertebrates, which diminish SR $Ca^{2+}$ uptake and myocyte contractility (Bers, 2002; MacLennan et al., 2003; Kranias and Hajjar, 2012; Anderson et al., 2015; Bal et al., 2012; Magny et al., 2013 and Dorn, 2004).

Defective intracellular calcium homeostasis is a hallmark of cardiac dysfunction, especially with regard to calcium reuptake and cycling during muscle contraction, but there are no treatments currently available that effectively enhance this pathway. Directly overexpressing the SERCA pump has proven difficult because of its large size and requirement of post-translational modification for function. Therefore, new methods of intervening in cytosolic $Ca^{2+}$ overload disorders is clearly needed.

SUMMARY

Thus, in accordance with the present disclosure, there is provided a method of promoting the activity of the SERCA calcium pump in a cell comprising contacting said SERCA pump with DWORF. DWORF may have the sequence of SEQ ID NO: 1, SEQ ID NO: 2, SEQ ID NO: 3, SEQ ID NO: 4. DWORF may be linked to apeptide or polypeptide segment, such as a cell permeability peptide, such as HIV TAT. DWORF may be as a peptide or polypeptide, or by expression of a nucleic acid segment coding for DWORF or a functional fragment thereof, said nucleic acid segment being under the control of a promoter active in eukaryotic cells, such as where the nucleic acid segment is provided as naked DNA or modified mRNA, or is provided in a viral particle, or is provided as a non-viral expression construct in a nanoparticle, microparticle or lipid vehicle. The method may further comprise contacting the SERCA calcium pump with a second SERCA activating agent, such as istaroxime.

The cell may be located in a living mammal, such as a non-human mammal, or a human. The contacting may occur at least a second time, such as on a chronic basis. DWORF may be provided to said mammal intravenously, intradermally, intraarterially, intraperitoneally, intranasally, topically, intramuscularly, subcutaneously, mucosally, intrapericardially, intraumbilically, orally, via injection, via infusion, via continuous infusion, via a catheter, via a lavage, in creams, or in lipid compositions (e.g., liposomes). The mammal may suffer from a disorder characterized by or comprised of cytosolic calcium overload, such as heart failure, restenosis or muscular dystrophy. In such case, the method may further comprise administering to said mammal a second therapy for heart failure, restenosis or muscular dystrophy.

Also provide is an isolated polypeptide comprising a sequence selected from the group consisting of wherein DWORF has the sequence of SEQ ID NO: 1, SEQ ID NO: 3, SEQ ID NO: 5, SEQ ID NO: 7 and SEQ ID NO: 9. The isolated polypeptide may be disposed in a pharmaceutically acceptable buffer, diluent or excipient. The isolated polypeptide may consist or consist essentially of SEQ ID NO: 1, SEQ ID NO: 3, SEQ ID NO: 5, SEQ ID NO: 7 and SEQ ID NO: 9. The isolated polypeptide may be linked to a heterologous peptide or polypeptide segment.

A further embodiment provides an isolated nucleic acid segment encoding a polypeptide comprising a sequence selected from the group consisting of wherein DWORF has the sequence of SEQ ID NO: 1, SEQ ID NO: 3, SEQ ID NO: 5, SEQ ID NO: 7 and SEQ ID NO: 9. The isolated nucleic acid segment may be disposed in a pharmaceutically acceptable buffer, diluent or excipient. The isolated nucleic acid segment may encode a polypeptide that consists or consists essentially of SEQ ID NO: 1, SEQ ID NO: 3, SEQ ID NO: 5, SEQ ID NO: 7 and SEQ ID NO: 9. The isolated nucleic acid segment may be linked to a heterologous nucleic acid segment, such as one that encodes a cell permeability peptide, such as HIV TAT, a promoter, an expression construct, such as a viral expression construct (e.g., an adenovirus construct, a retrovirus construct, a pox virus construct, or a herpesvirus construct), or a non-viral expression construct.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the disclosure, and vice versa. Furthermore, compositions and kits of the disclosure can be used to achieve methods of the disclosure.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Amino acid sequence alignment of vertebrate DWORF proteins. (FIG. 1B) Northern blot of adult mouse tissues showing DWORF RNA expression. (FIG. 1C) Detection of DWORF RNA by qPCR in adult mouse tissues. (FIG. 1D) Detection of DWORF RNA by qPCR in hearts of mice at the indicated ages. (FIG. 1E) The 5' UTR and the first thirteen codons of DWORF were cloned as an in-frame fusion with the HaloTag protein. The empty HaloTag vector lacks an initiation codon and is not translated. The DWORF 5' UTR is capable of initiating translation and can be detected by immunoblotting with an antibody for the HaloTag protein or an antibody against DWORF. (FIG. 1F) Western blot of adult mouse tissues with the DWORF antibody revealed a single band at the predicted size of 3.8 kDa. (FIG. 1G) Detection of DWORF RNA by qPCR in six month old WT and αMHC-calcineurin mice. (FIG. 1H) Western blot analysis of heart homogenates from WT and αMHC-calcineurin mice immunoblotted with DWORF antibody. (FIG. 1I) qPCR analysis of human ischemic heart failure tissue showing reduced DWORF mRNA in failing hearts while atrial natriuretic peptide (NPPA) is significantly increased.

(FIG. 2A) Two-photon scanning confocal microscopy of the flexor digitorum brevis muscle of adult mice after in vivo electroporation of plasmids encoding GFP-DWORF, GFP-PLN or GFP-SLN indicates SR localization of DWORF that mimics that of PLN and SLN. (M, M-line; Z, Z-line). (FIG. 2B) Co-localization of GFP-DWORF and mCherry-SERCA in transfected COS7 cells. (FIG. 2C) Co-immunoprecipitation experiments in transfected COS7 cells using GFP-DWORF and Myc-tagged SERCA isoforms. IP, Immunoprecipitation. (FIG. 2D) Immunoprecipitation of Myc-SERCA from lysates of COS7 cells transfected with equal amounts of HA-DWORF, -PLN, -SLN, or -MLN and Myc-SERCA with 5-fold overexpression of either GFP or GFP-DWORF. Co-expression of GFP-DWORF reduced the pulldown of HA-tagged peptides in association with SERCA indicating that DWORF binding to SERCA excludes binding of PLN, SLN or MLN. (FIG. 2E) Immunoprecipitation of Myc-SERCA in COST cells transfected with varying ratios of GFP-DWORF and GFP-PLN and detection with an antibody for GFP indicates that DWORF and PLN have similar binding affinities for SERCA.

(FIG. 3A) A CRISPR gRNA was generated to target the coding sequence of exon two. An allele containing a 2-bp insertion was chosen for further experiments. The mutation is expected to produce a truncated protein lacking the transmembrane domain. (FIG. 3B) Western blot showing the absence of DWORF protein in the cardiac ventricle and soleus muscle of DWORF knockout (KO) mice. (FIG. 3C) Representative $Ca^{2+}$ transients and SR load measurements recorded in fluo-4 loaded cardiomyocytes from WT, α-MHC-DWORF (Tg) and DWORF KO mice. (FIG. 3D) Mean amplitude of pacing-induced $Ca^{2+}$ transients in fluo-4 loaded cardiomyocytes from WT, Tg and KO mice and caffeine-induced $Ca^{2+}$ transients triggered by rapid application of 10 mM caffeine to quantify SR load. $Ca^{2+}$ signal is shown as fluorescence ratio ($F/F_0$) with the fluorescence intensity (F) normalized to the minimal intensity measured between 0.5 Hz contractions at diastolic phase ($F_0$). (FIG. 3E) Average decay time constants (Tau) of pacing-induced $Ca^{2+}$ transients in WT, Tg, and DWORF KO cardiomyocytes measured by fitting a single exponential to the $Ca^{2+}$ transient decay trace. This parameter is indicative of SERCA activity. (FIG. 3F) Mean values of decay time constants (Tau) of caffeine-induced $Ca^{2+}$ transients as a measure of $Na^+/Ca^{2+}$ exchanger (NCX) activity. (FIG. 3G) Representative pacing-induced fractional shortening traces in isolated cardiomyocytes stimulated at 0.5 Hz as measured by edge detection. Peak fractional shortening amplitude (FIG. 3H), peak systolic $Ca^{2+}$ transient amplitude (FIG. 3I), and systolic $Ca^{2+}$ transient decay rates (Tau) (J) of WT, Tg and KO mice measured at baseline and in response to 10 nM isoproterenol (Iso). (FIG. 3K) Isometric force was measured from soleus muscles mounted ex vivo and stimulated by 0.2 msec current pulses applied at a range of frequencies. Left: Force decay was slower in DWORF KO muscles (arrow) after fully fused tetanic contractions as shown for 90 Hz (inset). Right: Slower relaxation for DWORF KO muscles occurred for stimulus frequencies sufficient to produce twitch fusion (>20 Hz), however, unfused twitches at low frequency showed no difference in relaxation rates. P-value<0.05, n=6.

(FIG. 4A) $Ca^{2+}$-dependent $Ca^{2+}$-uptake assays were performed using total homogenates from hearts of WT, α-MHC-DWORF (Tg) and DWORF KO mice to directly measure SERCA affinity for $Ca^{2+}$ ($K_{Ca}$) and SERCA activity. Mean $K_{Ca}$ values from n=8 hearts of each genotype are represented as bar graphs. (FIG. 4B) $Ca^{2+}$-dependent $Ca^{2+}$-uptake assays were performed using total homogenates from soleus muscles of WT and DWORF KO mice. Mean $K_{Ca}$ values from n=8 mice of each genotype are represented as bar graphs. (C) Myocytes release $Ca^{2+}$ from the SR through the ryanodine receptor (RyR), which causes sarcomere contraction. For muscle relaxation, $Ca^{2+}$ must be transported back to the SR by SERCA. SERCA is inhibited by PLN. PLN inhibition is opposed by the small transmembrane peptide, DWORF, which increases activity of SERCA.

FIGS. 6A-B. Overview of the Dworf locus. (FIG. 6A) In mice, Dworf is transcribed from an unannotated 2.8 kb locus on chromosome 3 to produce two transcript isoforms of approximately 300 bp that only differ by inclusion of three additional base pairs, producing a polyadenylated RNA. The predicted open reading frame (highlighted in red) begins in exon one and ends near the 3' end of exon two. In humans the transcript is annotated as a lncRNA named LOC100507537 and appears to only produce a single isoform. (FIG. 6B) PhyloCSF plot of the Dworf locus as extracted and analyzed from 14 different mammalian species.

FIGS. 8A-C. Western blot analysis of heart tissue homogenates from αMHC-DWORF transgenic mice. (FIG. 8A) Extensive western blotting of heart homogenates from αMHC-DWORF transgenic mice reveals no significant changes in total expression or phosphorylation status of relevant $Ca^{2+}$ handling proteins as compared to wild-type mice. A second αMHC-DWORF transgenic line was also generated and is characterized in FIGS. 9A-C. (FIG. 8B) Immunoblots were quantified using ImageJ. Total protein westerns (RyR, LTCC, PMCA, SERCA, NCX and PLN) were normalized to GAPDH. (FIG. 8C) Phosphorylation blots (PS16 and PT17) were normalized to total PLN. RyR (ryanodine receptor 2), LTCC (α1C-subunit of the voltage regulated L-Type $Ca^{2+}$ channel), PMCA (plasma membrane $Ca^{2+}$-ATPase), SERCA2 (SR $Ca^{2+}$-ATPase 2), NCX ($Na^+$/$Ca^{2+}$-exchanger), PLN (phospholamban), PS16 (phospho-serine 16 on PLN), PT17 (phospho-threonine 17 on PLN), GAPDH (Glyceraldehyde 3-phosphate dehydrogenase).

FIGS. 9A-C. RT-PCR and Western analysis of heart and skeletal muscle from DWORF knockout mice. (FIG. 9A) DWORF mRNA is increased approximately four fold in the hearts of adult knockout mice, but other notable genes are not altered. *P-value=0.006. (FIGS. 9B-C) Extensive western blotting of $Ca^{2+}$ regulatory proteins in heart (FIG. 9B) and soleus muscle (FIG. 9C) homogenates from DWORF KO mice reveals no significant changes in total protein expression levels or phosphorylation status of relevant $Ca^{2+}$ handling proteins as compared to WT mice. Immunoblots were quantified using ImageJ. Westerns for total protein (RyR, LTCC, PMCA, SERCA, NCX and PLN) were normalized to GAPDH and phosphorylation blots (PS16 and PT17) were normalized to total PLN. RyR (ryanodine receptor 2), LTCC (α1C-subunit of the voltage regulated L-Type $Ca^{2+}$ channel), PMCA (plasma membrane $Ca^{2+}$-ATPase), SERCA2 (SR $Ca^{2+}$-ATPase 2), NCX ($Na^+$/$Ca^{2+}$-exchanger), PLN (phospholamban), PS16 (phospho-serine 16 on PLN), PT17 (phospho-threonine on PLN), GAPDH (Glyceraldehyde 3-phosphate dehydrogenase).

FIGS. 10A-C. Ca'-dependent Ca'-uptake assay in hearts and quadriceps muscles from αMHC-DWORF and DWORF KO mice. (FIG. 10A) A second αMHC-DWORF transgenic line (Tg Line 2) was generated with a more modest level of DWORF overexpression as assessed by DWORF immunoblotting of heart lysates. (FIG. 10B) SERCA activity was measured using the $Ca^{2+}$-dependent $Ca^{2+}$-uptake assay. This second transgenic line exhibited a leftward shift of the $Ca^{2+}$ affinity curve confirming that overexpression of DWORF results in elevated SERCA activity and a higher affinity for $Ca^{2+}$. Similar to the inventors' findings in their first transgenic line, modulating DWORF expression has no apparent effect on $V_{max}$. (FIG. 10C) $Ca^{2+}$-dependent $Ca^{2+}$-uptake assays measuring SERCA affinity for $Ca^{2+}$ was unchanged in quadriceps muscle of DWORF KO.

FIGS. 11A-B. Sequences for Mouse DWORF. (FIG. 11A) Depiction of splice variation and SNP found in DWORF protein sequences. (FIG. 11B) DWORF nucleotide sequences.

FIG. 12. Sequences for Human DWORF.

FIGS. 13A-C. DWORF overexpression rescues in vivo cardiac function in the muscle LIM protein (MLP) KO mouse model of dilated cardiomypathy. Transthoracic echocardiographic measurements of unanesthetized mice with the indicated genotypes. Ejection Fraction (FIG. 13A) and Fractional Shortening (FIG. 13B) parameters were calculated from M-mode electrocardiographic tracings (FIG. 13C) (* vs WT, # vs MLP KO).

FIGS. 14A-C. DWORF overexpression rescues pathological cardiac remodeling in MLP KO mice. Left ventricular (LV) dimesions were calculated from M-mode echochardiographic measurements and are presented as values during systole (peak contraction, LVIS, FIG. 14A) and diastole (relaxation, LVID, FIG. 14B). Heart weight to tibia length measurements were calculated from isolated tissues (FIG. 14C) and indicate that DWORF overexpression in MLP KO mice rescues the pathological remodeling seen in these animals (* vs WT, # vs MLP KO).

FIGS. 15A-B. DWORF overexpression rescues the ultra-structural defects and fibrotic phenotype of MLP KO mice. (FIG. 15A) Electron microscopic analysis of MLP KO hearts indicates severe myofibrilar disarray which is prevented by the overexpression of DWORF. (FIG. 15B) MLP KO hearts exhibit diffuse fibrosis (red color, picrosirium red stain) that is rescued when DWORF is overexpressed in the heart (DWORF Tg) of these animals.

DESCRIPTION OF ILLUSTRATIVE EMBODIMENTS

Figure 1:
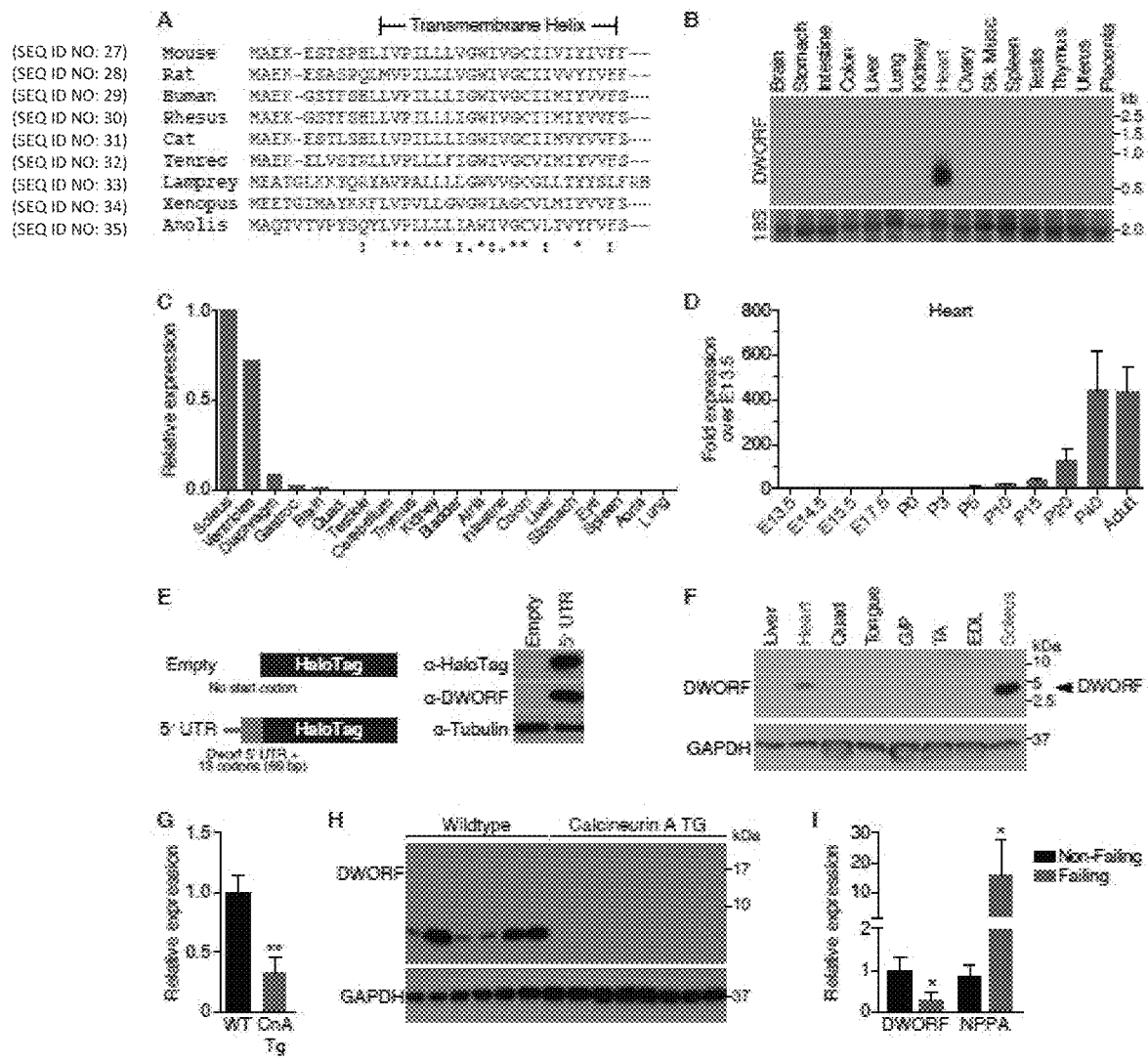
FIGS. 1A-I. Muscle-specific expression of DWORF.

As discussed above, there has been significant interest in increasing the activity of the SERCA calcium pump in the context of heart failure where decreased calcium release and resequestration weaken the ability of the heart to preserve contractile function and maintain adequate tissue perfusion and eventually results in disease progression and premature death. In rodent and large animal models of heart failure, over-expression of SERCA improves strength and endurance of the heart and ameliorates disease progression. For this reason, human clinical trials, named CUPID I and CUPID 2, were undertaken to evaluate the therapeutic potential of over-expressing SERCA in heart failure patients by viral gene delivery. Unfortunately, this trial was very recently reported to have failed in meeting its endpoints. Despite the unfortunate failure of this trial, there is still significant interest in boosting SERCA activity, though a final report on the trials is yet to be reported.

Here, the inventors report the isolation of a coding sequence for an endogenous transmembrane protein that enhances the apparent activity of the SERCA pump. Through interaction with the SERCA pump, this peptide (henceforth referred to as Dwarf Open Reading Frame or DWORF), increases muscle contractility and the rate of muscle relaxation, i.e., the peptide is positively inotropic and lusitropic. SERCA function is often dysregulated in heart failure leading to loss of contractility, relaxation, and cytosolic calcium overload. Because DWORF enhances calcium cycling kinetics, it is an attractive candidate for gene therapies that target calcium storage and clearance. Also, because DWORF is a very small peptide, only 34 amino acids, it may be more amenable to delivery methods with restricted payload capacity.

DWORF is an endogenous enhancer of SERCA calcium pump activity, a desirable drug target for regulation of cardiac contractility. DWORF is also an unusually small protein, which may facilitate delivery of the gene or protein to target tissues. Because DWORF is an endogenous protein, expression of DWORF in humans would not be immunogenic, allowing for long-term dosing and expression. Previous strategies to target the calcium handling machinery of the heart have focused on overexpression of the SERCA pump, which is decreased in heart failure. As outlined below, DWORF presents an attractive alternative therapeutic strategy for a number of reasons.

DWORF may be an attractive alternative to expression of SERCA for multiple reasons. First, although SERCA protein levels are decreased in heart failure, there is also an increase in a small transmembrane inhibitor of SERCA known as phospholamban. Therefore, expressing SERCA alone may not be sufficient to overcome the increased inhibition caused by phospholamban. Since DWORF can enhance the activity of SERCA in the presence of phospholamban, it may be more beneficial to increase the activity of the endogenous SERCA pump by expressing DWORF rather than the pump itself. Second, SERCA is a very large multi-pass transmembrane protein that is among the most abundantly expressed proteins in cardiac myocytes. These properties may make it very difficult to overexpress the protein, especially in cells that are already compromised, meaning that the therapeutic threshold for this protein may be quite high. On the other hand, DWORF is a very small protein that can be rapidly produced from a relatively small number of transcripts. DWORF is expressed at relatively low levels in the human myocardium (compared to rodents in which it is quite high), suggesting that the therapeutic threshold would be much lower than for SERCA. Lastly, it has been shown that SERCA2a (the cardiac isoform of the enzyme) requires post-translational modification with SUMO for full activity, a process that may be limited by the capacity for SUMOylation rather than SERCA abundance. Ectopic expression of DWORF could increase the activity of the available SERCA without the need to increase its abundance.

These and other aspects of the disclosure are discussed below.

I. SERCA

SERCA, or sarco/endoplasmic reticulum $Ca^{2+}$-ATPase, or SR $Ca^{2+}$-ATPase, is a calcium ATPase-type P-ATPase. SERCA resides in the sarcoplasmic reticulum (SR) within muscle cells. It is a $Ca^{2+}$ ATPase that transfers $Ca^{2+}$ from the cytosol of the cell to the lumen of the SR at the expense of ATP hydrolysis during muscle relaxation.

There are 3 major domains on the cytoplasmic face of SERCA: the phosphorylation and nucleotide-binding domains, which form the catalytic site, and the actuator domain, which is involved in the transmission of major conformational changes. The rate at which SERCA moves $Ca^{2+}$ across the SR membrane can be controlled by the regulatory protein phospholamban (PLB/PLN). SERCA is normally inhibited by PLB, with which it is closely associated. Increased β-adrenergic stimulation reduces the association between SERCA and PLB by the phosphorylation of PLB by PKA. When PLB is associated with SERCA, the rate of $Ca^{2+}$ movement is reduced; upon dissociation of PLB, $Ca^{2+}$ movement increases.

Another protein, calsequestrin, binds calcium within the SR and helps to reduce the concentration of free calcium within the SR, which assists SERCA so that it does not have to pump against such a high concentration gradient. The SR has a much higher concentration of $Ca^{2+}$ (10,000×) inside when compared to the cytoplasmic $Ca^{2+}$ concentration. SERCA2 can be regulated by microRNAs, for instance miR-25 suppresses SERCA2 in heart failure. For experimental reasons, SERCA can be inhibited by thapsigargin and induced by istaroxime.

There are 3 major paralogs, SERCA1-3, which are expressed at various levels in different cell types: ATP2A1-SERCA1, ATP2A2-SERCA2 and ATP2A3-SERCA3. There are additional post-translational isoforms of both SERCA2 and SERCA3, which serve to introduce the possibility of cell-type-specific $Ca^{2+}$-reuptake responses as well as increasing the overall complexity of the $Ca^{2+}$ signaling mechanism.

II. FAILURE OF CYTOSOLIC CALCIUM CLEARANCE IN CARDIAC AND SKELETAL MUSCLE DISEASES

In the heart, clearance of $Ca^{2+}$ during diastole is essential for relaxation and storage of $Ca^{2+}$ for successive contractions. As such, elevated end-diastolic $Ca^{2+}$ concentration leads to decreased cardiac performance and is a recognized feature of most forms of diastolic heart failure (Louch et al., 2012). Changes in expression of critical proteins and subcellular structure are thought to underlie defects in diastolic $Ca^{2+}$ clearance. Loss of T-tubules (a process also known as detubulation) is a documented phenomenon in advanced heart failure (Swift et al., 2012; Song et al., 2006; Louch et al., 2006; Heinzel et al., 2008). Detubulation leads to orphaned RyRs that can become asynchronous with the cardiac action potential because of the increased distance from DHPRs. Loss of the dyadic micro-domain also causes alteration of $Ca^{2+}$ uptake kinetics by SERCA (Brette et al., 2005). A number of changes in $Ca^{2+}$ handling genes have also been shown to be perturbed in the setting of heart failure, including SERCA, phospholamban, and NCX (Houser et al., 2000). Increases in the ratio of phospholamban to SERCA reduce the cell's ability to re-sequester $Ca^{2+}$ in the SR, which increases tension of the resting fiber and reduces contractile strength in subsequent contractions. Aberration of SERCA activity may lead to a greater reliance on NCX for $Ca^{2+}$ removal, but increased intracellular sodium, which also may occur in heart failure, diminishes the ability of NCX to remove $Ca^{2+}$ the cell. Therefore, restoration of SERCA activity using DWORF or genetic sequences encoding DWORF would have a foreseeably positive effect on cardiac contractility and by extension, morbidity and mortality of heart disease.

Restoration of SERCA activity by relieving phospholamban inhibition of the pump has previously been shown to have beneficial effects on cardiovascular function in a well characterized mouse model of dilated cardiomyopathy (DCM)(Arbor et al., 1999). Muscle LIM protein (MLP) is a structural protein involved in muscle development and structural integrity and a knockout mouse model of MLP leads to severe heart failure that can be completely rescued by knocking out phospholamban, which restores SERCA activity and calcium homeostasis (Minamisawa et al., 1999). Overexpression of DWORF has the same functional effect as removal of phospholamban, thereby presenting a very attractive therapeutic option for heart failure treatment.

Another scenario that results in increased cytosolic $Ca^{2+}$ retention occurs when blood flow is restored to a previously ischemic region of cardiac muscle. In this setting, reperfusion paradoxically results in further injury to the tissue, a phenomenon known as ischemia reperfusion injury. Introduction of molecules such as DWORF or genetic sequences encoding DWORF during arterial recanalization could hasten restoration of ionic homeostasis and reduce tissue injury.

Accumulation of cytosolic $Ca^{2+}$ has also been implicated in some skeletal muscle diseases, namely muscular dystrophies. It is hypothesized that loss of dystophin or other components of the dystrophin-glycoprotein complex results in chronic microscopic shredding of the sarcolemma or hyperactivity of stretch-activated channels. These events may allow $Ca^{2+}$ to leak into the cell and accumulate by overwhelming the $Ca^{2+}$ clearance machinery (Allen et al., 2010). It is thought that accumulation of $Ca^{2+}$ contributes significantly to dystrophic disease progression by promoting myofiber necrosis (Whitehead et al., 2006). This hypothesis is supported by the fact that overexpression of stretch-activated $Ca^{2+}$ channels in skeletal muscle results in a dystrophic phenotype (Millay et al., 2009). Recently deregulation of $Ca^{2+}$ by way of increased intracellular sodium and NCX over-activity were also shown to play a role in muscular dystrophy (Burr et al., 2014).

Alterations in $Ca^{2+}$ clearance have also been suggested as a contributing mechanism in physiologic fatigue of skeletal muscles, although this is among many other hypothesized causes (Allen et al., 2008). Recent work by Anderson et al. in which the skeletal muscle inhibitor of SERCA, myoregulin, was knocked out showed an increase in running endurance in the KO mice (Anderson et al., 2015). This work contributes further evidence that $Ca^{2+}$ handling plays a crucial role in the physiology of muscle fatigue. Given the importance of cytosolic $Ca^{2+}$ clearance in skeletal muscle, it is foreseeable that DWORF or genetic sequences encoding DWORF could be of benefit in reducing the morbidity and mortality of skeletal muscle diseases with features of cytosolic $Ca^{2+}$ retention.

Because of the involvement of SERCA in muscle diseases, it is hypothesized that increasing activity of SERCA, either by pharmacologic or gene-based therapy, might be an effective strategy. In mice, overexpression of SERCA1a using a transgene or adeno-associated virus in the muscles of dystrophic mice improved the severity of the disease (Goonasekera et al., 2011). Similarly, overexpression of SERCA2a in failing hearts of rodents, pigs, and sheep has been shown to improve heart function (del Monte et al., 2004; del Monte et al., 2001; Schmidt et al., 2000; Miyamoto et al., 2000; Hajjar et al., 1998; Byrne et al., 2008; Kawase et al., 2008 and Sakata et al., 2007). Because of the small size, low molecular complexity, and positive effects on SERCA activity of the DWORF protein, it is an ideal candidate molecule for treatment of diseases that are characterized by increased cytosolic calcium or reduced SERCA activity.

III. DWORF PEPTIDES AND POLYPEPTIDES AND NUCLEIC ACIDS CODING THEREFOR

A. DWORF Polypeptides

The DWORF polypeptide sequence is illustrated in SEQ ID NO: 1 (mouse) and SEQ ID NO: 3 (human). The mouse DWORF coding sequence is shown as SEQ ID NO: 2 (mouse) and SEQ ID NO: 4 (human). With only 34 codons, DWORF is the third smallest full-length protein known to be encoded by the mouse genome.

The mouse DWORF transcript is encoded by 3 exons on chromosome 3. The ORF begins in exon 1, which encodes the first four amino acids of the protein, and the remaining protein is encoded in exon 2. Alternative usage of two adjacent splice acceptor sequences between exons 1 and 2 produces two transcripts that differ by a 3 nucleotide insertion. Based on RNA-seq reads mapping to the exon junction, the shorter isoform of 34 amino acids appears to be substantially more abundant in the heart. The DWORF ORF is conserved to lamprey, the most distant extant vertebrate species for which a genome sequence is currently available and the ORF scores positively by PhyloCSF. The C-terminal region is enriched in hydrophobic amino acids and is predicted to encode a tail-anchored transmembrane peptide. The N-terminal region is less stringently conserved, but most sequences (except for that of *Anolis carolensis*) contain multiple charged residues (primarily lysine and aspartic acid) in this region.

B. DWORF Peptides

The present disclosure contemplates the design, production and use of various DWORF peptides. The structural features of these peptides are as follows. First, the peptides may have 5 to 35 consecutive residues of DWORF. Thus, the term "a peptide having no more than X consecutive residues," even when including the term "comprising," cannot be understood to comprise a greater number of consecutive DWORF residues. In general, the peptides will be 35 residues or less, again, comprising no more than 20 consecutive residues of DWORF. The overall length may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 residues. Ranges of peptide length of 5-34/35 residues, 6-34/35 residues, 7-50 residues, 7-25, residues, 5-20 residues, 6-20 residues, 7-20 residues, and 7-15 residues are contemplated. The number of consecutive DWORF residues may be 5, 6, 7, 8, 9, 10, 11, 12, 13, 14, 15, 16, 17, 18, 19 or 20. Ranges of consecutive residues of 5-20 residues, 5-20 residues, 6-20 residues, 7-20 residues and 5-15 residues, 5-15, residues, 6-15 residues or 7-15 residues are contemplated.

The present disclosure may utilize an L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally-occurring polypeptides involves the synthetic assemblage of amino acids with .alpha.-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present disclosure contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length), while others are shown in Table 1, below.

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

1. Synthesis

It may be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the disclosure are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

2. Linkers

Linkers or cross-linking agents may be used to fuse DWORF peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., *J. American Chemical Soc.*, 2000, 122(24): p. 5891-5892.

C. Purification

In certain embodiments, the polypeptide and peptides of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

D. Nucleic Acids and Expression

In certain embodiments, DWORF may be delivered to a SERCA pump or a subject via nucleic acid that is expressed in a eukaryotic expression system. Expression cassettes are employed to express DWORF after delivery to a cell/subject, i.e., for use directly in a genetic-based delivery approach, and also for in vitro synthesis and subsequent purification of the protein. Expression requires that appropriate signals be provided in the vectors, and include various regulatory elements such as enhancers/promoters from both viral and mammalian sources that drive expression of the genes of interest in cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Nucleic acids according to the present disclosure may encode all of DWORF, a domain of DWORF that stimulates SERCA, or any other fragment of DWORF. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present disclosure may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given DWORF from a given species may be represented by natural variants that have slightly different nucleic acid sequences but, nonetheless, encode the same protein (see discussion in the Examples, below).

As used in this application, the term "a nucleic acid encoding a DWORF" refers to a nucleic acid molecule that has been isolated free of total cellular nucleic acid. In certain embodiments, the disclosure concerns a nucleic acid sequence essentially as set forth in the sequence listing. The term "functionally equivalent codon" is used herein to refer to codons that encode the same amino acid, such as the six codons for arginine or serine, and also refers to codons that encode biologically equivalent amino acids, as discussed in the following pages.

Allowing for the degeneracy of the genetic code, sequences that have at least about 50%, usually at least about 80%, preferably at least about 90% and most preferably about 95% of nucleotides that are identical to the nucleotides of the sequences set forth in the sequence listing. Sequences that are essentially the same as those set forth in sequence listing also may be functionally defined as sequences that are capable of hybridizing to a nucleic acid segment containing the complement of the sequences set forth in the sequence listing under standard conditions.

The DNA segments of the present disclosure include those encoding biologically functional equivalent DWORF proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

1. Regulatory Elements

Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| 3-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |

TABLE 2-continued

Promoter and/or Enhancer

| Promoter/Enhancer | References |
| --- | --- |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987a |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2-κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the α-actin promoter (Moss et al., 1996), the troponin 1 promoter (Bhaysar et al., 1996); the $Na^+/Ca^{2+}$ exchanger promoter (Barnes et al., 1997), the dystrophin promoter (Kimura et al., 1997), the α7 integrin promoter (Ziober and Kramer, 1996), the brain natriuretic peptide promoter (LaPointe et al., 1996) and the αB-crystallin/small heat shock protein promoter (Gopal-Srivastava, 1995), α-myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the disclosure, and any such sequence may be employed such as human growth hormone and SV40 polyadenylation signals. Also contemplated as an element of the expression cassette is a terminator. These elements can serve to enhance message levels and to minimize read through from the cassette into other sequences.

2. Delivery of Expression Vectors

There are a number of ways in which expression vectors may introduced into cells. In certain embodiments of the disclosure, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the disclosure. The adenovirus may be of any of the 42 different known serotypes or subgroups A-F. Adenovirus type 5 of subgroup C is the preferred starting material in order to obtain the conditional replication-defective adenovirus vector for use in the present disclosure. This is because Adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the disclosure. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present disclosure. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present disclosure. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present disclosure. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the disclosure, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the disclosure for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present disclosure.

In a further embodiment of the disclosure, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection. A reagent known as Lipofectamine 2000™ is widely used and commercially available.

In certain embodiments of the disclosure, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

3. Modified mRNAs

Another approach for gene expression employs synthetic modified RNA sequences, and in particular for in vivo protein expression in tissues and organs, and also in cells in vivo, e.g., muscle cells including but not limited to cardiomyocytes and myogenic cells. Other aspects relate to use of modified-RNAs encoding DWORF for treatment of diseases and disorders, for example, but not limited to muscle disorders and cardiovascular diseases and disorders in a subject. Other aspects relate to pharmaceutical compositions and kits thereof comprising a least one synthetic modified-RNA encoding DWORF for administration to a subject for treatment of diseases or disorders in a subject. In some embodiments, the disease or disorder is a cardiovascular disease or disorder.

Recently, it has been reported that synthetic, modified RNA (herein referred to as "MOD-RNA") can be used for overexpression of a gene of interest in mammalian cells in vitro. The chemical and sequence modifications made in the synthetic mRNA stabilize the molecule and enhance transcription. Expression of polypeptides from MOD-RNA allows for highly efficient, transient expression of a gene of interest in vitro without requiring introduction of DNA or viral sequences that may be integrated into the host cell. Demonstrated delivery of synthetic modified RNAs using tailored transfection techniques, and in some embodiments, administration of MOD-RNAs in a composition can also comprise specific reagents that inhibit degradation of an introduced, synthetic modified RNA. WO 2012138453 A1 provides supporting information on such techniques.

IV. THERAPIES

A. Heart Failure and Diseases Characterized by Cytosolic $Ca^{2+}$ Retention

There are many causes of heart failure syndromes, but they generally result in inability of the cardiac muscle to provide sufficient perfusion to tissues, resulting in systemic ischemia and fluid accumulation. All heart failure patients have similar symptoms, but failure can result from multiple etiologies, most being related to insufficiency of contractile strength, relaxation to allow for filling, or a combination of both features. Calcium handling is vital to both of these etiologies of heart failure. For the scenario of impaired contractility, internal calcium stores of the myocyte are typically insufficient or release from the SR is dampened either because of damage to the microarchitecture of the myocyte or kinetic dysfunction of the calcium storage and release machinery. Diastolic failure can have similar molecular origins, but ultimately results in delayed clearance of calcium following contraction, which results in incomplete relaxation. The SERCA pump is the only route for calcium to be re-sequestered back to the SR following contraction, and dysfunctional SERCA expression or activity has been extensively linked to heart failure syndromes. Since DWORF modulates the activity of the SERCA pump, it would be a rational therapy for heart failure.

In addition to heart failure, DWORF is also contemplated for use in decreasing reperfusion injury following coronary artery catherization to treat a myocardial infarction. Reperfusion injury is a paradoxical further injury to ischemic tissue following restoration of blood flow, i.e., reperfusion. It is thought that this phenomenon is caused by influx of calcium and sodium during reperfusion, which then leads to hypercontraction, activation of proteolytic enzymes and metabolic stress. Administration of DWORF or its genetic code by viral or MOD-RNA during catheterization could potentially limit the extent of this type of very common injury.

Finally, DWORF may also used as a treatment for muscular dystrophy. Although far less common than heart failure or coronary disease, MD causes a significant morbidity and mortality for those affected. In Duchenne muscular dystrophy models, excessive calcium influx results in damage similar to that described for reperfusion injury. It is reasonable to predict that DWORF could treat this disease.

B. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render agents stable and allow for uptake by target cells. Aqueous compositions of the present disclosure comprise an effective amount of the agents to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the agents of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intracardiac, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

C. Methods of Treatment

In particular, the compositions described above are preferably administered to a mammal (e.g., rodent, human, non-human primates, canine, bovine, ovine, equine, feline, etc.) in an effective amount, that is, an amount capable of producing a desirable result in a treated subject (e.g., reducing cytosolic calcium overload). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of cancer and other drugs being administered concurrently. A composition as described herein is typically administered at a dosage and route that stimulates SERCA. In some embodiments, amounts of the agents used are calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease associated with cytosolic calcium overload, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

D. Combination Therapies

It is envisioned that the peptides/peptoids described herein may be used in combination therapies with an additional therapeutic agent or regimen. It is very common in the field of medicine to combine therapeutic modalities, both for increased efficacy, and reduction of dosages and hence side effects. The following is a general discussion of therapies that may be used in conjunction with the therapies of the present disclosure.

To treat diseases or disorders characterized by cytosolic calcium overload using the methods and compositions of the present disclosure, one would generally contact a subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the peptides/peptoids described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a DWORF therapy is "A," and the other SERCA-based therapy is "B," as exemplified below:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are also contemplated.

Istaroxime is an investigational drug now under development for treatment of acute decompensated heart failure. It is still in early-stage development, having been evaluated in phase two clinical trials. Istaroxime is an effective treatment for both systolic and diastolic heart failure. Systolic heart failure is characterized by impaired ventricular emptying, caused by reduced contractility, and diastolic dysfunction is defined by defective ventricular filling, caused by the heart's inability to properly relax between beats. Intracellular calcium fluxes regulate both contraction and relaxation. Cardiac muscle cells from patients with heart failure show smaller amounts of peak calcium in their cytoplasm during contraction, and slower removal. The mishandling of intracellular calcium is often due to problems in the cells' ability to mediate calcium influx, and sequestration of calcium back in the sarcoplasmic reticulum.

Istaroxime is a positive inotropic agent that mediates its action through inhibition of sodium/potassium adenosine triphosphatase ($Na^+/K^+$ ATPase). $Na^+/K^+$ ATPase inhibition increases intracellular sodium levels, which reverses the driving force of the sodium/calcium exchanger, inhibiting calcium extrusion and possibly facilitating calcium entry. Additionally, Istaroxime increases intracellular calcium by improving the efficacy by which intracellular calcium triggers sarcoplasmic reticulum calcium release, and by accelerating the inactivation state of L-type calcium channels, which allow for calcium influx. Together the changes in calcium handling increase cell contraction.

Istaroxime also enhances the heart's relaxation phase by increasing the rate of intracellular calcium sequestration by Sarco/endoplasmic Reticulum Calcium ATPase, isotype 2a (SERCA2a). SERCA2a is inhibited by phospholamban and higher phospholamban-to-SERCA2a ratios cause SERCA inhibition and impaired relaxation. Istaroxime reduces SERCA2a-phospholamban interaction, and increases SERCA2a affinity for cytosolic calcium. Studies on failing human heart tissue show that Istaroxime increases SERCA2a activity up to 67%.

Clinical trials show that Istaroxime improves ejection fraction, stroke volume and systolic blood pressure, while also enhancing ventricular filling. The drug also reduces heart rate and ventricular diastolic stiffness. Contrary to available inotropic therapies, Istaroxime may permit cytosolic calcium accumulation while avoiding a proarrhythmic state. Proposed mechanisms for Istaroxime's antiarrhythmic effect include a suppression of the transient inward calcium current directly involved in the production of delayed afterdepolarizations and improved calcium sequestration due to SERCA2a stimulation. SERCA down-regulation in the failing myocardium might sensitize patients to the detrimental effect of other currently used positive inotropes. Istaroxime's lusitropic effect facilitates its wider margin of safety, as patients can receive higher doses without signs of arrhythmias.

Thapsigargin is non-competitive inhibitor of the sarco/endoplasmic reticulum $Ca^{2+}$ ATPase (SERCA). Structurally, thapsigargin is classified as a sesquiterpene lactone, and is extracted from a plant, *Thapsia garganica*. It is a tumor promoter in mammalian cells. Thapsigargin raises cytosolic (intracellular) calcium concentration by blocking the ability of the cell to pump calcium into the sarcoplasmic and endoplasmic reticula. Store-depletion can secondarily activate plasma membrane calcium channels, allowing an influx of calcium into the cytosol. Thapsigargin specifically inhibits the fusion of autophagosomes with lysosomes; the last step in the autophagic process. The inhibition of the autophagic process in turn induces stress on the endoplasmic reticulum which ultimately leads to cellular death.

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Identification of Conserved Small Open Reading Frames. Total RNA was extracted from adult mouse heart tissue using Trizol (Invitrogen). An RNA sequencing library was prepared using the TruSeq RNA Library Prep Kit (Illumina) according to the manufacturer's protocol. Reads were mapped to the UCSC mm9 reference genome (Kent et al., 2002) using TopHat (Trapnell et al., 2009). Final transcripts were assembled using Cufflinks and consolidated with the mm9 reference annotations (Trapnell et al., 2012). Novel transcripts (i.e., those not existing in the reference annotation) were extracted and combined with transcripts annotated as long non-coding RNA in the UCSC database. Sequence alignments from fourteen mammalian species (mouse, rabbit, rat, human, chimpanzee, rhesus monkey, shrew, dog, cat, horse, cow, armadillo, elephant, and tenrec) were extracted using the "Stitch Gene blocks" tool in Galaxy (Blankenberg et al., 2011; Giardine et al., 2005; Blankenberg et al., 2010 and Goecks et al., 2010). PhyloCSF was used to calculate conservation scores for potential ORFs in three frames on both strands (Lin et al., 2011). Only the highest scoring ORF for each transcript was reported.

Quantitative mRNA Measurement. Total RNA was extracted from adult mouse tissues using Trizol and reverse transcribed using the SuperScript III First-Strand Synthesis System (Invitrogen) with a 1:1 mix of random hexamer and oligo-dT primers. Quantitative Polymerase Chain Reaction (qPCR) was performed using 5' nuclease assays on the StepOne Real-Time PCR System (Life Technologies). The following oligonucleotides were ordered from Integrated DNA Technologies to measure endogenous DWORF abundance:

```
Forward
                               (SEQ ID NO: 11)
5'-TTCTTCTCCTGGTTGGATGG-3';

Reverse
                               (SEQ ID NO: 12)
5'-TCTTCTAAATGGTGTCAGATTGAAGT-3';

Probe
                               (SEQ ID NO: 13)
5'-TTTACATTGTCTTCTTCTAGAAAAGGAAGAAG-3'.
```

Probes were labeled with 5' 6-FAM, an internal ZEN quencher, and a 3' Iowa Black quencher and used in a 2:1 ratio with primers. Human cDNAs were quantified using SYBR Green with the following primers:

```
Forward
                               (SEQ ID NO: 14)
5'-CCACCCACCAACAGGAATA-3';

Reverse
                               (SEQ ID NO: 15)
5'-TTATGATGCAGCCCACAATC-3'.
```

Each sample was normalized to a Eukaryotic 18S rRNA Endogenous Control (Life Technologies) reaction.

Northern Blot Analysis. A DWORF cDNA fragment was PCR purified from heart RNA extract with the following primers:

```
Forward
                               (SEQ ID NO: 16)
5'-TTTCCAAAAGATAGGAAATACTACAGC-3';

Reverse
                               (SEQ ID NO: 17)
5'-ACTCCTGGCCCTGACTAAGC-3'.
```

The fragment was gel purified and cloned into the TOPO pCR2.1 plasmid (Life Technologies). Following amplification in *E. coli*, the probe template was excised with EcoRI and gel purified. Radiolabeled probe was prepared using the RadPrime DNA Labeling System (Life Technologies) with $\alpha$-$^{32}$P-dCTP. Radiolabeled probe was hybridized overnight at 68° C. to a commercial northern blot (Zyagen, MN-MT-1) containing 20 µg of total RNA per sample. The hybridized blot was washed four times and then exposed to autoradiography film for twenty-four hours. The blot was then stripped using a published protocol and probed for the 18S rRNA loading control using the same procedure described for DWORF.

Antibody Derivation. A custom polyclonal antibody was derived against the N-terminal region of the predicted DWORF protein by New England Peptide. Rabbits were immunized with a synthetic peptide with the following sequence—MAEKESTSPHLIC (SEQ ID NO: 18). Sera were collected and affinity purified against the peptide immunogen.

Human Heart Failure Tissue. Samples were acquired from the Temple University human heart tissue bank (IRB #21319). All ischemic heart failure samples were core biopsies of post-MI heart failure patients at the time of transplant. An n of 8 was used for both failing and non-failing hearts.

Western Blot Analysis. Lysates were prepared by pulverizing snap frozen tissues in liquid nitrogen and then homogenizing in RIPA buffer (150 mM NaCl; 1% v/v Igepal CA-630; 50 mM Tris-Cl, pH 8.3; 0.5% w/v sodium deoxycholate; 0.1% w/v sodium dodecyl sulfate) with added protease inhibitors (cOmplete ULTRA mini tablet, Roche) on ice using a 'tight' glass dounce homogenizer. Protein concentrations were determined using a BCA Protein Assay Kit (Pierce). For DWORF and PLN, samples were separated on a 16.5% tricine buffered polyacrylamide gel (BioRad). Samples for other experiments were separated on Any kD tris-glycine buffered polyacrylamide gels (BioRad). DWORF was electroblotted onto Immobilon P$^{SQ}$ membranes (Millipore) using a semi-dry apparatus for 30 min at 20 V. Other experiments were electroblotted onto Immobilon P membranes using a semi-dry apparatus for 50 min at 20 V. Membranes were blocked overnight at 4° C. in blotto (5% w/v non-fat dry milk in TBST). Primary antibody hybridization was carried out overnight at 4° C. with the following antibodies: DWORF, 1:5,000; total PLN (2D12, Pierce), 1:5,000; pSer$^{16}$-PLN (Badrilla), 1:5,000; pThr$^{17}$-PLN (Badrilla), 1:5,000; SERCA2 (2A7-A1, Pierce), 1:2000; NCX1 (Abcam), 1:500; RyR2 (Pierce, C3-33), 1:1000; LTCC (Millipore, α1C), 1:1000; PMCA (Pierce, 5F10), 1:250; GAPDH (Millipore); 1:10,000. Blots were washed five times for five minutes each, in TBST and then incubated with HRP-conjugated secondary antibodies (Bio-Rad) at 1:20,000. Blots were then developed with chemiluminescent substrate and exposed to either autoradiograph film or a digital ChemiDoc system (G:BOX, GeneSys).

Generation of Mouse Lines. All experiments involving animals were approved by the Institutional Animal Care and Use Committee at the University of Texas Southwestern Medical Center. Knockout mice were generated using the CRISPR/Cas9 system by pronuclear and cytoplasmic injection of mouse embryos with guide RNA (gRNA) and Cas9 mRNA as described previously (Long et al., 2014). Briefly, a gRNA was cloned that targeted the predicted coding sequence of DWORF. Cleavage efficiency was tested in cell culture, and then the gRNA and Cas9 mRNA were transcribed in vitro and spin-column purified. Mouse embryos were injected with an equal ratio of gRNA and Cas9 mRNA into the pronucleus and cytoplasm and then transferred to a surrogate dam for gestation. Because F$_0$ founders are expected to be mosaic, allelic disruption was confirmed in the F$_0$ generation pups using the T7E1 endonuclease assay on tail biopsies, and positive founders were bred to wild-type C57/BL6 mice to isolate potential knockout alleles. Mutants in the F$_1$ generation were identified by T7E1 assay and then the alleles were cloned and sequenced. One mouse line with a two-bp insertion was chosen for further study.

Transgenic mice were derived by pronuclear injection of mouse embryos. Briefly, the DWORF coding sequence was cloned into an αMHC promoter-driven plasmid with a polyadenylation sequence from the human growth hormone (hGH) gene. The plasmid was injected into the pronucleus of mouse embryos and then implanted in a surrogate dam for gestation. F$_0$ generation pups were selected by presence of transgene by PCR from a tail biopsy and bred to wild-type. F$_1$ generation pups were bred to C57/BL6 mice and expression of the transgene was verified in the F2 progeny by qPCR.

Genotyping of Mouse Lines. Knockout mice were genotyped using a custom TaqMan genotyping assay (Life Technologies). Briefly, tail biopsies were digested in lysis buffer (50 mM KCl; 10 mM Tris-Cl, pH 8.3; 2.5 mM MgCl$_2$; 0.1 mg/mL porcine gelatin; 0.45% v/v Igepal CA-630; 0.45% v/v Tween 20) with proteinase K (6 U/mL) overnight at 55° C. Particulates were removed by high-speed centrifugation, and the supernatant was diluted 1:10 in water. The tail samples were then analyzed by qPCR with a mixture of the following oligonucleotides:

```
Forward Primer
                                 (SEQ ID NO: 19)
5'-TCATTGCTTCTAAGCAGAGTCAACA-3';

Reverse Primer
                                 (SEQ ID NO: 20)
5'-ATGCAGCCTACAATCCATCCAA-3';

WT Probe
                                 (SEQ ID NO: 21)
5'-CCAGGAGAAGAATG-3';

KO Probe
                                 (SEQ ID NO: 22)
5'-CAGGAGACAAGAATG-3'.
```

Transgenic mice were genotyped based on presence or absence of the hGH sequence. Tail biopsies were processed as described for the DWORF KO mice, and used for PCR with a 1:1:1:1 mixture of the following primers (myogenin primers are used as a positive control):

```
hGH Forward Primer
                                 (SEQ ID NO: 23)
5'-GTCTGACTAGGTGTCCTTCT-3';

hGH Reverse Primer
                                 (SEQ ID NO: 24)
5'-CGTCCTCCTGCTGGTATAG-3';

Myogenin Forward Primer
                                 (SEQ ID NO: 25)
5'-TTACGTCCATCGTGGACAGC-3';

Myogenin Reverse Primer
                                 (SEQ ID NO: 26)
5'-TGGGCTGGGTGTTAGCCTTA-3'.
```

PCR products were analyzed by agarose gel electrophoresis.

Co-immunoprecipitations (CoIPs). CoIPs were performed as described in detail (Anderson et al., 2009). HEK 293 cells or COST cells were transfected with GFP-DWORF, GFP-PLN, HA-DWORF, HA-PLN, HA-SLN, HA-MLN and Myc-tagged SERCA. Immunoprecipitations were carried out using mouse anti-GFP (Life Technologes) or mouse anti-Myc antibody (Invitrogen) and collected with Dynabeads (Life Technologies). Standard western blot procedures were performed on IP fractions using HRP-conjugated GFP (Pierce, GF28R), Myc (Pierce, 9E10) or HA (Pierce, 2-2.2.14) antibodies.

Mouse Cardiomyocyte Isolation. Adult mouse myocytes were isolated as described (Makarewich et al., 2014 and Jaleel et al., 2008). Anesthesia was induced using 3% isoflurane and maintained using 1% isoflurane. Mouse hearts were rapidly excised and the aorta was cannulated on a constant-flow Langendorff apparatus. The heart was digested by perfusion of Tyrode's solution containing 0.2 mg/mL Liberase DH (Roche), 0.14 mg/mL Trypsin (Gibco/Invitrogen) and (mM): CaCl$_2$ 0.02, glucose 10, HEPES 5, KCl 5.4, MgCl$_2$ 1.2, NaCl 150, sodium pyruvate 2, pH 7.4. When the tissue softened, the left ventricle was isolated and gently minced, filtered, and equilibrated in Tyrode's solution with 200 μM CaCl$_2$, and 1% bovine serum albumin (BSA) at room temperature.

Ca$^{2+}$ Transients and SR Load. Myocytes were loaded with 5 μM fluo-4 AM (Molecular Probes) and placed in a heated chamber (35° C.) on the stage of an inverted microscope and perfused with Tyrode's solution containing in mM: CaCl$_2$) 1, glucose 10, HEPES 5, KCl 5.4, MgCl$_2$ 1.2, NaCl 150, sodium pyruvate 2, pH 7.4. Myocytes were paced at 0.5 Hz and fractional shortening data was collected using edge detection. For intracellular $Ca^{2+}$ fluorescence measurements, the $F_0$ (or F unstimulated) was measured as the average fluorescence of the cell 50 ms prior to stimulation. The maximal fluo-4 fluorescence (F) was measured at peak amplitude. Background fluorescence was subtracted from each parameter before representing the peak $Ca^{2+}$ transient as $F/F_0$ (Makarewich et al., 2014 and Jaleel et al., 2008). Tau (τ) was measured as the decay rate of the average $Ca^{2+}$ transient trace. Isoproterenol (Iso, Sigma) was used at 10 nM.

To measure SR $Ca^{2+}$ content, myocytes were paced at 0.5 Hz for 10 consecutive contractions, and 10 mM caffeine (Sigma) was then rapidly applied via a glass pipette close to the myocyte with a Pico spritzer (Piacentino et al., 2003). The decay of caffeine-induced $Ca^{2+}$ transients was fit with a single-exponential function, and time constant (τ) values indicate $Na^+/Ca^{2+}$-exchanger (NCX) activity.

Oxalate-Supported $Ca^{2+}$ Uptake Measurements. Oxalate-supported $Ca^{2+}$ uptake in cardiac homogenates was measured by a modified Millipore filtration technique (Piacentino et al., 2003; Luo et al., 1994; Holemans et al., 2014 and Anderson et al., 2015). Heart, soleus and quadriceps tissues were isolated from WT, Tg and KO mice and rapidly frozen in liquid nitrogen and stored at −80° C. until processed. Frozen tissue samples were homogenized in 50 mM phosphate buffer, pH 7.0 containing 10 mM NaF, 1 mM EDTA, 0.3 M sucrose, 0.3 mM PMSF and 0.5 mM DTT. $Ca^{2+}$ uptake was measured in reaction solution containing 40 mM imidazole pH 7.0, 95 mM KCl, 5 mM $NaN_3$, 5 mM $MgCl_2$, 0.5 mM EGTA, 5 mM $K^+$ oxalate, 1 μM ruthenium red and various concentrations of $CaCl_2$ to yield 0.02 to 5 μM free $Ca^{2+}$. Homogenates were incubated at 37° C. for 2 minutes in the above reaction buffer and the reaction was initiated by the addition of ATP (final concentration 5 mM). The data were analyzed by nonlinear regression with computer software (GraphPad Software), and the $K_{Ca}$ values were calculated using an equation for a general cooperative model for substrate activation. The values for maximal SERCA activity were taken directly from the experimental data and normalized for total protein concentration (μmol/mg protein/min). Statistical analyses were performed using an unpaired t-test and data are presented as mean±SEM.

Contractile force of soleus muscle. The soleus muscle was dissected free and suspended in an organ bath maintained at 37° C. One end was tied to a rigid post and the other was fastened to a force transducer (Myobath, WPI Inc.). Isometric contractions were elicited by application of brief current pulses of 0.2 msec duration at 80 mA (A385 Stimulator; WPI Inc.). Low frequency pulse trains (<10 Hz) elicited unfused twitch responses and progressively higher stimulation frequencies produced a smooth tetanic contraction. Contraction tests were separated by a 2 minute rest interval to prevent fatigue. Muscle contraction was quantified as the peak force and the time constant for relaxation that was obtained from a single exponential fit to the decay in force from 50% of the maximum back to baseline. The bath contained 118 mM NaCl, 4.7 mM KCl, 1.18 mM $MgSO_4$, 2.5 mM $CaCl_2$, 1.18 mM $NaH_2PO_4$, 10 mM glucose, 24.8 mM $NaHCO_3$ and was continuously bubbled with 95% O2 and 5% $CO_2$. d-turbocurarine (0.25 μM) was added to prevent muscle activation from nerve fiber endings.

Skeletal Muscle Electroporation. Flexor digitorum brevis muscles were electroporated with GFP-tagged constructs and visualized fresh in physiologic buffer using two-photon laser scanning microscopy as described previously (DiFranco 2009; Nelson et al., 2013).

Transthoracic Echocardiography. Cardiac function and heart dimensions were determined by two-dimensional echocardiography using a Visual Sonics Vevo 2100 Ultrasound (Visual Sonics, Canada) on nonanesthetized mice. M-mode tracings were used to measure anterior and posterior wall thicknesses at end diastole and end systole. Left ventricular (LV) internal diameter (LVID) was measured as the largest anteroposterior diameter in either diastole (LVIDd) or systole (LVIDs). A single observer blinded to mouse genotypes performed echocardiography and data analysis. Fractional shortening (FS) was calculated according to the following formula: FS (%)=[(LVIDd−LVIDs)/LVIDd]×100. Ejection fraction (EF %) was calculated by: EF (%)=EDV-ESV/EDV (ESV; end systolic volume, EDV; end diastolic volume).

Transmission electron microscopy. Hearts were fixed by perfusion with 4% paraformaldehyde and 1% glutaraldehyde in 0.1 M sodium cacodylate buffer (pH 7.4). Samples were processed by the University of Texas Southwestern Medical Center Electron Microscopy Core facility. Briefly, fixed tissues were post-fixed, stained, dehydrated, and embedded in EMbed-812 resin. Tissue sections were cut and post-stained, and images were acquired on a FEI Tecnai $G^2$ Spirit TEM.

Example 2—Results

Figure 5:
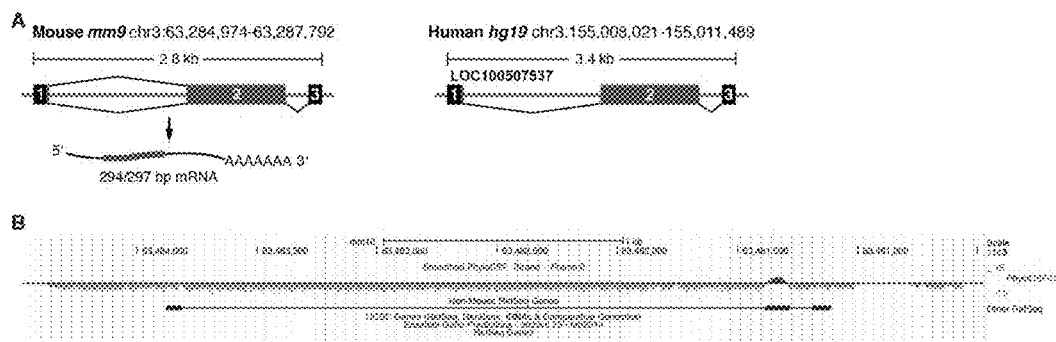
FIG. 5. Dworf cDNA sequence from mouse. Nucleotide sequence of a cloned fragment of Dworf from mouse heart cDNA. The ORF is highlighted in red with the amino acid sequence below.

Recently, the inventors discovered MLN as a small open reading frame (ORF) hidden in a transcript annotated as a long non-coding RNA (lncRNA) (Anderson et al., 2015). They hypothesized that many transcripts currently annotated as lncRNAs may encode small proteins that have evaded gene annotation attempts and recent proteomic analyses support this notion (Slavoff et al., 2013; Frith et al., 2006 and Nelson et al., 2014). To identify potential muscle-specific micropeptides, the inventors searched bioinformatically using PhyloCSF for putative ORFs within mouse transcripts annotated as lncRNAs (Lin et al., 2011). Among these RNAs, they discovered a previously unrecognized muscle-specific RNA containing a potential ORF of 34 codons, which the inventors called Dwarf Open Reading Frame (DWORF) (FIG. 1A and FIG. 5). The DWORF RNA transcript is annotated as NONCODE lncRNA gene NON-MMUG026737 (Xie et al., 2014) in mice and lncRNA gene LOC100507537 in the UCSC human genome (FIG. 6A). With only 34 codons, DWORF is the third smallest full-length protein known to be encoded by the mouse genome.

The mouse DWORF transcript is encoded by 3 exons on chromosome 3 (FIG. 6A). The ORF begins in exon 1, which encodes the first four amino acids of the protein, and the remaining protein is encoded in exon 2. Alternative usage of two adjacent splice acceptor sequences between exons 1 and 2 produces two transcripts that differ by a 3 nucleotide insertion. Based on RNA-seq reads mapping to the exon junction, the shorter isoform of 34 amino acids appears to be substantially more abundant in the heart. The DWORF ORF is conserved to lamprey, the most distant extant vertebrate species for which a genome sequence is currently available (FIG. 1A) and the ORF scores positively on PhyloCSF (FIG. 6B). The C-terminal region is enriched in hydrophobic amino acids and is predicted to encode a tail-anchored transmembrane peptide (Sonnhammer et al., 1998; Krogh et al., 2001 and Goujon et al., 2010). The N-terminal region is less stringently conserved, but most sequences (except for that of *Anolis carolensis*) contain multiple charged residues (primarily lysine and aspartic acid) in this region. Unless otherwise stated, further studies focused on the mouse homolog.

Northern blot analysis showed that the DWORF mRNA transcript is robustly expressed in the heart (FIG. 1B). By quantitative RT-PCR, DWORF RNA was also detected in heart and soleus, a postural muscle group of the hindlimb that contains the greatest enrichment of slow-twitch muscle fibers in mice (FIG. 1C), as well as diaphragm, which contains some slow-twitch fibers but is primarily a fast-twitch muscle in mice (Guido et al., 2010 and Schiaffino and Reggiani, 2011). Notably, DWORF was not detected in the quadriceps, a fast-twitch muscle group, or in cardiac atrial muscle. DWORF is not expressed in the prenatal heart, but gradually increases in abundance post-natally (FIG. 1D).

To verify that the DWORF transcript encodes a protein, the inventors cloned the predicted 5' untranslated region (UTR) including the first thirteen codons of the DWORF RNA into a HaloTag expression vector that contains a protein tag but lacks a Kozak sequence and start codon. Expression of the empty and DWORF-containing constructs in non-muscle cells (COST) followed by western blot analysis with an antibody against the HaloTag protein showed that the full-length fusion protein was expressed as expected, demonstrating that the DWORF 5' UTR is capable of initiating translation (FIG. 1E). To confirm that the DWORF transcript encodes a protein, the inventors raised a polyclonal rabbit antibody against the N-terminal 12 amino acids of the predicted mouse DWORF protein. Western blot analysis revealed a single band at the expected molecular weight of 3.8 kDa in soleus and heart, but not in other tissues (FIG. 1F).

Given its abundance in the heart, the inventors examined whether the expression of DWORF mRNA or protein changed in response to pathological cardiac signaling. Indeed, in mice bearing an αMHC-Calcineurin A (CnA) transgene, which serve as a model of hypertrophic heart disease that progresses to dilated cardiomyopathy by six months of age (Molkentin et al., 1998), DWORF mRNA was down-regulated in dilated transgenic hearts of six month-old mice (FIG. 1G). The level of DWORF protein was even more dramatically down-regulated in these hearts (FIG. 1H). DWORF mRNA was also down-regulated in ischemic failing human hearts, linking changes in DWORF expression with human cardiomyopathies (FIG. 1I) (Makarewich et al., 2015).

Figure 2:
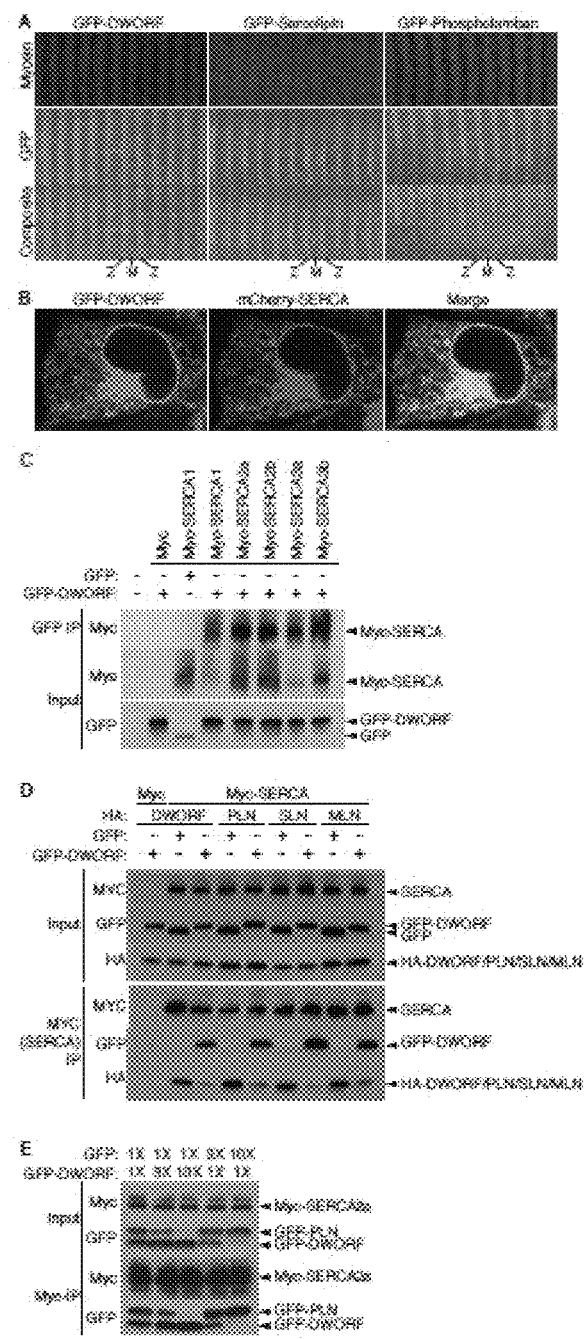
FIGS. 2A-E. SR localization and association of DWORF with SERCA.

The inventors investigated the subcellular distribution of DWORF in skeletal muscle fibers by electroporation of a GFP-DWORF expression vector into the flexor digitorum brevis muscle of the mouse foot (Nelson et al., 2013). Live imaging analysis using two-photon excitation microscopy to simultaneously visualize GFP and myosin (using second harmonic generation) showed that GFP-DWORF localized in an alternating pattern with myosin (FIG. 2A), a distribution resembling the location of the SR. GFP-SLN and GFP-PLN were individually expressed in the flexor digitorum brevis muscle for comparison. The visible co-localization of GFP-DWORF, GFP-SLN and GFP-PLN was striking, demonstrating notable transverse and lengthwise striations typical of longitudinal SR. The subcellular distribution of GFP-DWORF in transfected COS7 cells also overlapped with that of mCherry-SERCA1 in the endoplasmic reticulum (ER) and peri-nuclear regions (FIG. 2B).

Figure 7:
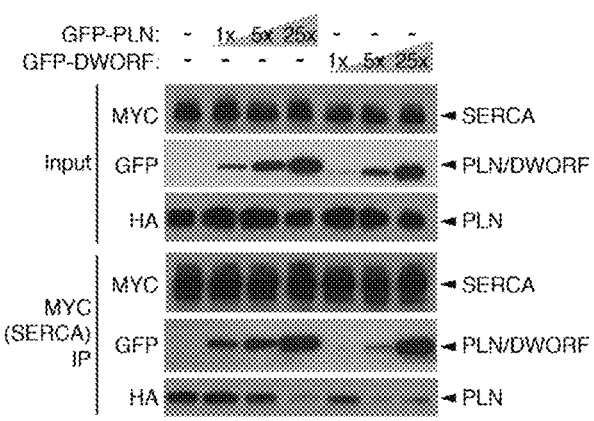
FIG. 7. DWORF binding to SERCA displaces PLN in a dose-dependent manner. Immunoprecipitation of Myc-SERCA from lysates of COS7 cells co-transfected with equal amounts of HA-PLN and Myc-SERCA and increasing amounts of either GFP-PLN or GFP-DWORF. Western blots on input samples and bound immunoprecipitated fractions reveal that DWORF binding to SERCA competitively displaces PLN from SERCA. GFP-PLN is used as a positive control for HA-PLN displacement.

Because GFP-DWORF co-localizes to the SR with SERCA, the inventors tested whether the two proteins physically interact. COS7 cells were co-transfected with GFP or GFP-DWORF and Myc-tagged SERCA1, 2a, 2b, 3a, or 3b. Immunoprecipitation with a GFP antibody co-precipitated GFP-DWORF with all isoforms of SERCA, but did not pull down SERCA in GFP transfected samples lacking DWORF (FIG. 2C). The inventors next examined whether co-expression of DWORF with SERCA would affect complex formation between SERCA and PLN, SLN, or MLN. Indeed, they observed a reduction in the binding of HA-PLN, -SLN, and -MLN with SERCA when co-expressed with GFP-DWORF (FIG. 2D and FIG. 7), suggesting that binding of DWORF and PLN to SERCA are mutually exclusive. Co-expression of Myc-SERCA2a with various ratios of GFP-DWORF and GFP-PLN followed by immunoprecipitation with anti-Myc and immunoblotting with anti-GFP indicated that DWORF and PLN have similar binding affinities for SERCA (FIG. 2E).

To assess the functions of DWORF in vivo, the inventors generated mouse models of gain and loss of DWORF function. DWORF over-expression in the heart was achieved by expressing untagged DWORF under the control of the cardiomyocyte-specific α-myosin heavy chain (αMHC) promoter in transgenic mice. Two transgenic founders that overexpressed the protein were selected for further studies. Other proteins involved in $Ca^{2+}$ handling were largely unaffected in these transgenic mice (FIGS. 8A-C).

Figure 3:
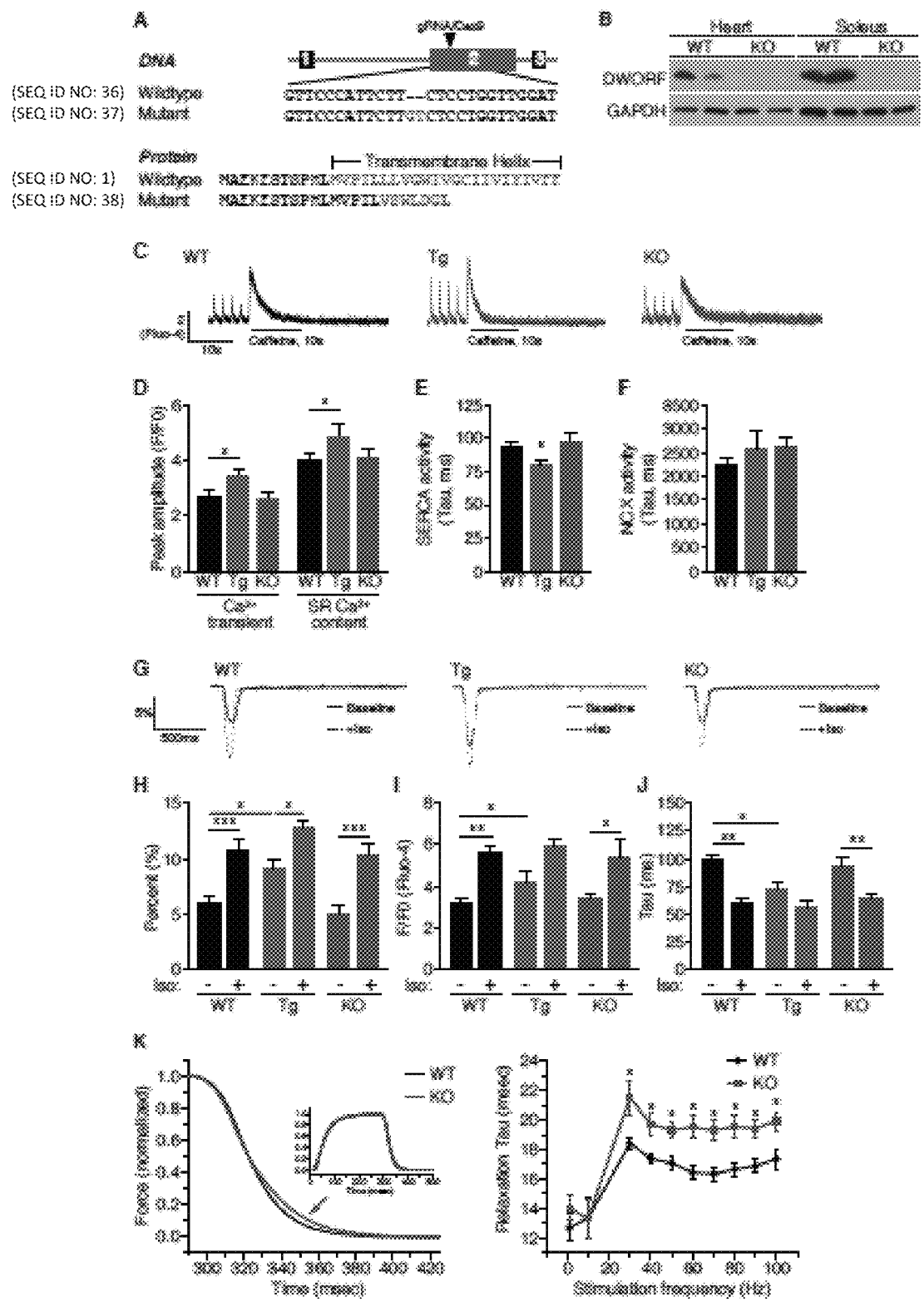
FIGS. 3A-K. Consequences of DWORF gain and loss of function.

The inventors used the CRISPR/Cas9 system to disrupt the coding frame of the DWORF protein in mice. A single guide RNA (gRNA) was designed to target the coding sequence of exon 2 before the transmembrane region (FIG. 3A). $F_0$ pups were screened for indels and a founder with a two-base-pair insertion that disrupts the ORF after codon 16 was chosen for further analysis. Breeding of heterozygous DWORF knockout (KO) mice yielded homozygous mutant offspring at expected Mendelian ratios. DWORF KO mice were phenotypically normal and displayed no obvious phenotype up to 1 year of age. Western blots of ventricular and soleus muscle probed with anti-DWORF antibody showed that the DWORF protein was completely eliminated in muscle tissues of homozygous mutant mice (FIG. 3B). Surprisingly, the DWORF transcript was up-regulated ~4-fold in the DWORF KO tissue (FIG. 9A), suggesting a potential feedback mechanism to enhance DWORF expression. Several notable RNA transcripts were not changed in DWORF KO mice, including those encoding the $Ca^{2+}$-handling proteins SERCA2 and PLN and the cardiac stress markers Myh7 and atrial natriuretic peptide (Nppa). Western blot analysis of heart (FIG. 9B) and soleus muscle (FIG. 9C) homogenates revealed no detectable changes in protein expression level or phosphorylation state of major $Ca^{2+}$-handling proteins.

The inventors examined whether $Ca^{2+}$ flux was altered in adult cardiomyocytes from WT, αMHC-DWORF Tg and DWORF KO mice using the fluorescent $Ca^{2+}$ indicator dye, fluo-4. Isolated cardiomyocytes were loaded with fluo-4, mounted on a temperature controlled perfusion chamber, and electrically stimulated at 0.5 Hz to initiate intracellular $Ca^{2+}$ transients which were monitored by epifluorescence. Peak systolic $Ca^{2+}$ transient amplitude and SR $Ca^{2+}$ load were significantly increased in Tg myocytes (FIGS. 3C-D). The pacing-induced $Ca^{2+}$ transient decay rate was also significantly enhanced in the Tg myocytes (FIG. 3E), suggesting that SERCA is more active in these cells. The decay rate of caffeine-induced $Ca^{2+}$ transients was unchanged in Tg myocytes, which indicates that the activity of the $Na^+/Ca^{2+}$ exchanger (NCX) is not altered (FIG. 3F). Tg myocytes had higher baseline measurements of contractility as measured by fractional shortening (FIGS. 3G-H), peak $Ca^{2+}$ transient amplitude (FIG. 3I), and $Ca^{2+}$ transient decay rate (FIG. 3J) and responded less strongly to beta-adrenergic stimulation by isoproterenol, likely because they are functioning at close to maximally active levels under baseline conditions. In the absence of increased protein abundance of SERCA or changes in other known $Ca^{2+}$ handling proteins, these findings indicate that SERCA activity is increased in muscle cells over-expressing DWORF.

The effect of DWORF ablation on skeletal muscle contractile function was assessed by measuring twitch force at multiple stimulation frequencies in isolated soleus muscles from WT and KO mice (Tupling et al., 2011). The inventors did not observe significant differences in peak muscle force between genotypes and saw no differences in relaxation rates at low, non-tetanic stimulation frequencies; however, at tetanus-inducing frequencies, relaxation rates were significantly slowed in DWORF KO muscles following tetanus (FIG. 3K). The effect on post-tetanic relaxation times may suggest that DWORF expression is particularly beneficial for recovery from prolonged contraction and $Ca^{2+}$ release.

Figure 4:
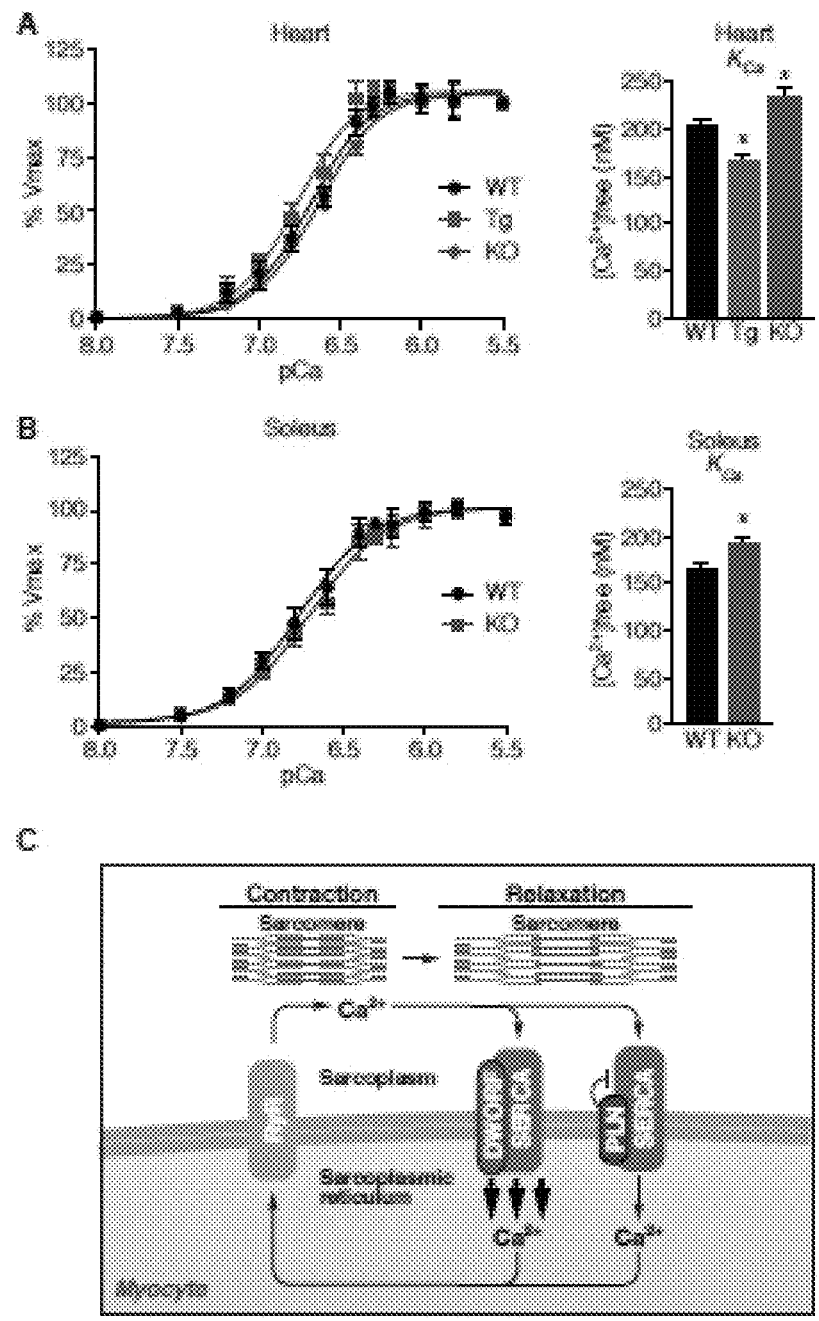
FIGS. 4A-C. Effect of DWORF on SERCA activity measured in $Ca^{2+}$-dependent $Ca^{2+}$-uptake assays and working model.

Oxalate-supported $Ca^{2+}$-dependent $Ca^{2+}$-uptake measurements in muscle homogenates provide a direct measurement of SERCA enzymatic activity (Tupling et al., 2011 and Davis et al., 1983). The inventors used this technique to measure SERCA activity in hearts of WT, Tg and KO mice. Hearts over-expressing DWORF showed an apparent increase in SERCA activity at lower concentrations of $Ca^{2+}$ substrate in both of the inventors' transgenic lines quantified as a higher affinity of SERCA for $Ca^{2+}$ (reduction in $K_{Ca}$) and DWORF KO hearts exhibited a less obvious but still significant decrease in the affinity of SERCA for $Ca^{2+}$ as indicated by an increase in $K_{Ca}$ (FIG. 4A, FIGS. 10A-B, and Table S1) The inventors did not observe changes in the maximal rate of $Ca^{2+}$ pump activity ($V_{max}$) in any of the inventors' genotypes (Table S1). Because DWORF is most abundant in the slow-twitch soleus muscle group, they also measured SERCA activity in soleus homogenates from WT and KO mice and used quadriceps muscles as a control, since DWORF is not expressed in this muscle group. The soleus muscle of DWORF KO mice showed a decreased apparent affinity for $Ca^{2+}$ compared to WT muscles (FIG. 4B and Table S2). These differences were not observed in quadriceps muscle (FIG. 9C and Table S3).

Based on gain and loss of function studies, these results demonstrate that DWORF enhances SR $Ca^{2+}$ uptake and myocyte contractility (FIG. 4C). Because DWORF can displace the inhibitory peptides PLN, MLN and SLN from SERCA, the inventors speculate that this mechanism represents the basis for its stimulatory influence on SERCA. However, it is also conceivable that DWORF acts through additional mechanisms and that the changes the inventors observed in $Ca^{2+}$ dynamics are secondary to some other process that DWORF regulates. Because DWORF increases the activity of the SERCA pump, it represents an attractive means of enhancing cardiac contractility in settings of heart disease. These findings show that cardiac-specific overexpression of DWORF (DWORF TG) in a mouse model of dilated cardiomyopathy (Muscle LIM protein knockout mice, (MLP KO)) leads to an enhancement of SERCA activity and a profound rescue of the heart failure phenotype seen in these animals (FIG. 13-15). Finally, these results underscore the likelihood that many transcripts currently annotated as non-coding RNAs encode micropeptides with important biological functions and that these micropeptides may have evolved as singular protein domains that exert their function by directly modulating the activities of larger regulatory proteins

TABLE S1

$Ca^{2+}$-dependent $Ca^{2+}$-uptake assay $K_{Ca}$ and $V_{max}$ values in total heart homogenates

| Genotype | $K_{Ca}$ (µM) | p-value | $V_{max}$ (nmol/mg/min) | p-value |
|---|---|---|---|---|
| WT | 0.2038 ± 0.0067 | NA | 62.81 ± 10.26 | NA |
| Tg Line 1 | 0.1670 ± 0.0072 | 0.0013 | 64.59 ± 5.81 | 0.824 |
| Tg Line 2 | 0.1810 ± 0.0078 | 0.0279 | 63.25 ± 9.34 | 0.887 |
| KO | 0.2328 ± 0.0110 | 0.0478 | 66.15 ± 5.77 | 0.687 |

TABLE S2

$Ca^{2+}$-dependent $Ca^{2+}$-uptake assay $K_{Ca}$ and $V_{max}$ values in total soleus muscle homogenates

| Genotype | $K_{Ca}$ (µM) | p-value | $V_{max}$ (nmol/mg/min) | p-value |
|---|---|---|---|---|
| WT | 0.1663 ± 0.0058 | NA | 16.07 ± 1.33 | NA |
| KO | 0.1923 ± 0.0086 | 0.0478 | 14.72 ± 1.84 | 0.688 |

TABLE S3

$Ca^{2+}$-dependent $Ca^{2+}$-uptake assay $K_{Ca}$ and $V_{max}$ values in total quadriceps homogenates

| Genotype | $K_{Ca}$ (µM) | p-value | $V_{max}$ (nmol/mg/min) | p-value |
|---|---|---|---|---|
| WT | 0.1782 ± 0.0119 | NA | 44.64 ± 4.83 | NA |
| KO | 0.1809 ± 0.0047 | 0.8446 | 48.98 ± 3.91 | 0.511 |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

U.S. Pat. No. 5,889,155
U.S. Pat. No. 6,261,569
U.S. Pat. No. 7,183,059
U.S. Pat. No. 7,192,713
Allen et al., Can J Physiol Pharmacol, 88(2): p. 83-91, 2010.
Allen et al., Physiol Rev, 88(1): p. 287-332, 2008.
Alluri et al., J. Am. Chem. Soc. 125:13995-4004, 2003.
Anderson et al., Cell 160:595-606, 2015.
Anderson et al., Dev Dyn 238:572-580, 2009.
Ando et al., Cell Immunol., 124:132-43, 1989.
Angel et al., Cell, 49:729, 1987b.
Angel et al., Mol. Cell. Biol., 7:2256, 1987a.
Arbor et al., Cell, 88:93-403, 1999.

Baichwal and Sugden, In: *Gene Transfer*, Kucherlapati (Ed), NY, Plenum Press, 117-148, 1986.
Bal et al., *Nat Med* 18:1575-1579, 2012.
Banerji et al., *Cell*, 27(2 Pt 1):299-308, 1981.
Banerji et al., *Cell*, 33(3):729-740, 1983.
Barnes et al., *J. Biol. Chem.*, 272(17):11510-7, 1997.
Benvenisty and Neshif, *Proc. Natl. Acad. Sci. USA*, 83:9551-9555, 1986.
Berkhout et al., *Cell*, 59:273-282, 1989.
Bers, *Nature* 415:198-205, 2002.
Bhaysar et al., *Genomics*, 35(1):11-23, 1996.
Blanar et al., *EMBO J.*, 8:1139, 1989.
Blankenberg et al., *Bioinformatics* 27:2426-2428, 2011.
Blankenberg et al., *Curr Protoc Mol Biol* Chapter 19, Unit 19 10 11-21, 2010.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Braun et al., *Arthritis Rheum.*, 42:2039-44, 1999.
Brette et al., *J Mol Cell Cardiol*, 39(5): p. 804-12, 2005.
Bulla and Siddiqui, *J. Virol.*, 62:1437, 1986.
Burr et al., *Mol Cell Biol*, 34(11): p. 1991-2002, 2014.
Byrne et al., *Gene Ther*, 15(23): p. 1550-7, 2008.
Calin et al., In: *The Spondylarthritides*, Calin et al. (Eds.), Oxford, UK. Oxford University Press, 179, 1998.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Celander and Haseltine, *J. Virology*, 61:269, 1987.
Celander et al., *J. Virology*, 62:1314, 1988.
Chandler et al., *Cell*, 33:489, 1983.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7:2745-2752, 1987.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Cook et al., *Cell*, 27:487-496, 1981.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
Davis et al., *J Biol Chem* 258:13587-13591, 1983.
De Villiers et al., *Nature*, 312(5991):242-246, 1984.
del Monte et al., Circulation, 104(12): p. 1424-9, 2001.
del Monte et al., *Proc Natl Acad Sci USA*, 101(15): p. 5622-7, 2004.
Deschamps et al., *Science*, 230:1174-1177, 1985.
DiFranco et al., *J Vis Exp*, 2009.
Dorn, Circulation 109:150-158, 2004.
Dubensky et al., *Proc. Natl. Acad. Sci. USA*, 81:7529-7533, 1984.
Edbrooke et al., *Mol. Cell. Biol.*, 9:1908, 1989.
Edlund et al., *Science*, 230:912-916, 1985.
EP 0273085
Fechheimer et al., *Proc Natl. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Fire et al., *Nature*, 391:806-811, 1998.
Firestein et al., *Arthritis Rheum.*, 37:644-52, 1994.

Fischer, *Med. Res. Rev.*, 27(6):755-796, 2007.
Foecking and Hofstetter, *Gene*, 45(1):101-105, 1986.
Forster and Symons, *Cell*, 49:211-220, 1987.
Fraley et al., *Proc Natl. Acad. Sci. USA*, 76:3348-3352, 1979
Franz et al., *Cardoscience*, 5(4):235-43, 1994.
Friedmann, *Science*, 244:1275-1281, 1989.
Frith et al., *PLoS Genet* 2:e52, 2006.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Giardine et al., *Genome Res* 15:1451-1455, 2005.
Gilles et al., *Cell*, 33:717, 1983.
Gloss et al., *EMBO J.*, 6:3735, 1987.
Godbout et al., *Mol. Cell. Biol.*, 8:1169, 1988.
Goecks et al., *Genome Biol* 11:R86, 2010.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Goonasekera et al., *J Clin Invest*, 121(3): p. 1044-52, 2011.
Gopal, *Mol. Cell Biol.*, 5:1188-1190, 1985.
Gopal-Srivastava et al., *J. Mol. Cell. Biol.*, 15(12):7081-90, 1995.
Goujon et al., *Nucleic Acids Res* 38:W695-699, 2010.
Goverman et al., *Cell*, 72:551-60, 1993.
Graham and Prevec, In: *Methods in Molecular Biology: Gene Transfer and Expression Protocol*, Murray (Ed.), Humana Press, Clifton, N.J., 7:109-128, 1991.
Graham and van der Eb, *Virology*, 52:456-467, 1973.
Graham et al., *J. Gen. Virol.*, 36:59-72, 1977.
Greene et al., *Immunology Today*, 10:272, 1989
Grosschedl and Baltimore, *Cell*, 41:885, 1985.
Grunhaus and Horwitz, *Seminar in Virology*, 3:237-252, 1992.
Guido et al., *Anat Rec* 293:1722-1728, 2010.
Hajjar et al., Proc Natl Acad Sci USA, 95(9): p. 5251-6, 1998.
Han et al., *Cancer Research*, 60:6068-6074, 2000.
Harland and Weintraub, *J. Cell Biol.*, 101:1094-1099, 1985.
Haslinger and Karin, *Proc. Natl. Acad. Sci. USA*, 82:8572, 1985.
Hauber and Cullen, *J. Virology*, 62:673, 1988.
Heinzel et al., Circ Res, 102(3): p. 338-46, 2008.
Hermonat and Muzycska, *Proc. Nat'l Acad. Sci. USA*, 81:6466-6470, 1984.
Herr and Clarke, Cell, 45:461, 1986.
Hersdorffer et al., *DNA Cell Biol.*, 9:713-723, 1990.
Herz and Gerard, Proc. Nat'l. Acad. Sci. USA 90:2812-2816, 1993.
Hirochika et al., *J. Virol.*, 61:2599, 1987.
Holbrook et al., *Virology*, 157:211, 1987.
Holemans et al., *Cold Spring Harb Protoc* 2014:876-886, 2014.
Horlick and Benfield, *Mol. Cell. Biol.*, 9:2396, 1989.
Horwich et al., *J. Virol.*, 64:642-650, 1990.
Houser et al., J Mol Cell Cardiol, 32(9): p. 1595-607, 2000.
Huang et al., *Cell*, 27:245, 1981.
Hug et al., *Mol. Cell. Biol.*, 8:3065, 1988.
Hwang et al., *Mol. Cell. Biol.*, 10:585, 1990.

Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Jakobovits et al., *Mol. Cell. Biol.,* 8:2555, 1988.
Jaleel et al., *Circ res* 103:1109-1119, 2008.
Jameel and Siddiqui, *Mol. Cell. Biol.,* 6:710, 1986.
Jarvis, *Curr Opin Rheumatol.,* 10:459-467, 1998.
Jarvis, *Pediatr Ann.,* 31:437-446, 2002.
Jaynes et al., *Mol. Cell. Biol.,* 8:62, 1988.
Johnson et al., *Mol. Cell. Biol.,* 9:3393, 1989.
Jones and Shenk, Cell, 13:181-188, 1978.
Jones et al., *Br. J. Rheumatol.,* 33:834-9, 1994.
Kadesch and Berg, *Mol. Cell. Biol.,* 6:2593, 1986.
Kaneda et al., *Science,* 243:375-378, 1989.
Karin et al., *Mol. Cell. Biol.,* 7:606, 1987.
Karlsson et al., *EMBO J.,* 5:2377-2385, 1986.
Katinka et al., *Cell,* 20:393, 1980.
Kato et al., *J Biol Chem.,* 266(6):3361-3364, 1991.
Kawamoto et al., *Mol. Cell. Biol.,* 8:267, 1988.
Kawase et al., J Am Coll Cardiol, 51(11): p. 1112-9, 2008.
Kelly et al., *J. Cell Biol.,* 129(2):383-96, 1995.
Kent et al., *Genome Res* 12:996-1006, 2002.
Kiledjian et al., *Mol. Cell. Biol.,* 8:145, 1988.
Klamut et al., *Mol. Cell. Biol.,* 10:193, 1990.
Klein et al., *Nature,* 327:70-73, 1987.
Koch et al., *Mol. Cell. Biol.,* 9:303, 1989.
Kranias and Hajjar, *Circ res* 110:1646-1660, 2012.
Kriegler and Botchan, In: *Eukaryotic Viral Vectors,* Gluzman (Ed.), Cold Spring Harbor: Cold Spring Harbor Laboratory, N Y, 1982.
Kriegler and Botchan, *Mol. Cell. Biol.,* 3:325, 1983.
Kriegler et al., *Cell,* 38:483, 1984.
Kriegler et al., *Cell,* 53:45, 1988.
Krogh et al., *J Mol Biol* 305:567-580, 2001.
Kuboyama, *Kurume Med. J.,* 45(1):33-37, 1998.
Kuhl et al., *Cell,* 50:1057, 1987.
Kunz et al., *Nucl. Acids Res.,* 17:1121, 1989.
LaPointe et al., *J. Biol. Chem.,* 263(19):9075-8, 1988.
Larsen et al., *Proc. Natl. Acad. Sci. USA.,* 83:8283, 1986.
Laspia et al., *Cell,* 59:283, 1989.
Latimer et al., *Mol. Cell. Biol.,* 10:760, 1990.
Le Gal La Salle et al., *Science,* 259:988-990, 1993.
Lee et al., *Nature,* 294:228, 1981.
Leiper et al., *Baillieres Clin. Gastroenterol.,* 12(1):179-99, 1998.
Levinson et al., *Nature,* 295:79, 1982.
Levrero et al., *Gene,* 101:195-202, 1991.
Lin et al., *Bioinformatics* 27:i275-282, 2011.
Lin et al., *Bioinformatics* 27:i275-282, 2011.
Lin et al., *Mol. Cell. Biol.,* 10:850, 1990.
Long et al., *Science* 345:1184-1188, 2014.
Louch et al., J Physiol, 574(Pt 2): p. 519-33, 2006.
Louch et al., Physiology (Bethesda), 27(5):p. 308-23, 2012
Luo et al., *J. Biol. Chem.,* 280:12668-12675, 2005.
Luria et al., *EMBO J.,* 6:3307, 1987.
Lusky et al., *Mol. Cell. Biol.,* 3:1108, 1983.
MacLennan et al., *Ann NY Acad Sci* 986:472-480, 2003.
Magny et al., *Science* 341:1116-1120, 2013.
Majors and Varmus, *Proc. Natl. Acad. Sci. USA,* 80:5866, 1983.
Makarewich et al., *Circ res* 115:567-580, 2014.
Makarewich et al., *J Mol Cell Cardiol* 86:179-186, 2015.
Mann et al., *Cell,* 33:153-159, 1983.
Markowitz et al., *J. Virol.,* 62:1120-1124, 1988.
McNeall et al., *Gene,* 76:81, 1989.
Miksicek et al., *Cell,* 46:203, 1986.
Millay et al., *Proc Natl Acad Sci USA,* 106(45): p. 19023-8, 2009.
Minamisawa et al., *Cell,* 99:313-322, 1999.
Miyamoto et al., *Proc Natl Acad Sci USA,* 97(2): p. 793-8, 2000.
Molkentin et al., *Cell* 93:215-228, 1998.
Mordacq and Linzer, *Genes and Dev.,* 3:760, 1989.
Moreau et al., *Nucl. Acids Res.,* 9:6047, 1981.
Moss et al., *J. Gen. Physiol.,* 108(6):473-84, 1996.
Muesing et al., *Cell,* 48:691, 1987.
Nelson et al., *Circ res* 114:18-20, 2014.
Nelson et al., *Proc Natl Acad Sci USA* 110:11881-11886, 2013.
Ng et al., *Nuc. Acids Res.,* 17:601, 1989.
Nicolas and Rubinstein, In: *Vectors: A survey of molecular cloning vectors and their uses,* Rodriguez and Denhardt (Eds.), Stoneham: Butterworth, 494-513, 1988.
Nicolau and Sene, *Biochim. Biophys. Acta,* 721:185-190, 1982.
Nicolau et al., *Methods Enzymol.,* 149:157-176, 1987.
Olson, *Science,* 313:1922-1927, 2006.
Ondek et al., *EMBO J.,* 6:1017, 1987.
Ornitz et al., *Mol. Cell. Biol.,* 7:3466, 1987.
Palmiter et al., *Cell,* 29:701, 1982.
Palmiter et al., *Nature,* 300:611, 1982.
Paskind et al., *Virology,* 67:242-248, 1975.
Pech et al., *Mol. Cell. Biol.,* 9:396, 1989.
Perales et al., *Proc. Natl. Acad. Sci. USA,* 91(9):4086-4090, 1994.
Perez-Stable and Constantini, *Mol. Cell. Biol.,* 10:1116, 1990.
Piacentino et al., *Circ res* 92:651-658, 2003.
Picard and Schaffner, *Nature,* 307:83, 1984.
Pinkert et al., *Genes and Dev.,* 1:268, 1987.
Ponta et al., *Proc. Natl. Acad. Sci. USA,* 82:1020, 1985.
Porton et al., *Mol. Cell. Biol.,* 10:1076, 1990.
Potter et al., *Proc. Natl. Acad. Sci. USA,* 81:7161-7165, 1984.
Queen and Baltimore, *Cell,* 35:741, 1983.
Quinn et al., *Mol. Cell. Biol.,* 9:4713, 1989.
Racher et al., *Biotech. Techniques,* 9:169-174, 1995.
Ragot et al., *Nature,* 361:647-650, 1993.
Rantapaa-Dahlqvist et al., *Arthritis Rheum.,* 48(10):2741-2749, 2003.
Redondo et al., *Science,* 247:1225, 1990.
Reisman and Rotter, *Mol. Cell. Biol.,* 9:3571, 1989.
Remington's Pharmaceutical Sciences, 15th ed., 1035-1038 and 1570-1580, Mack Publishing Company, P A, 1980.
Renan, *Radiother. Oncol.,* 19:197-218, 1990.
Resendez Jr. et al., *Mol. Cell. Biol.,* 8:4579, 1988.
Rich et al., *Hum. Gene Ther.,* 4:461-476, 1993.
Ridgeway, In: *Vectors: A survey of molecular cloning vectors and their uses,* Stoneham: Butterworth, 467-492, 1988.
Ripe et al., *Mol. Cell. Biol.,* 9:2224, 1989.
Rippe et al., *Mol. Cell Biol.,* 10:689-695, 1990.
Rittling et al., *Nuc. Acids Res.,* 17:1619, 1989.
Rosen et al., *Cell,* 41:813, 1988.
Rosenfeld et al., *Cell,* 68:143-155, 1992.
Rosenfeld et al., *Science,* 252:431-434, 1991.
Sakai et al., *Genes and Dev.,* 2:1144, 1988.
Sakata et al., J Mol Cell Cardiol, 42(4): p. 852-61, 2007.
Satake et al., *J. Virology,* 62:970, 1988.
Schaffner et al., *J. Mol. Biol.,* 201:81, 1988.

Schiaffino and Reggiani, *Physiol Rev* 91:1447-1531, 2011.
Schmidt et al., Circulation, 101(7): p. 790-6, 2000.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Slavoff et al., *Nat Chem Biol* 9:59-64, 2013.
Sleigh and Lockett, *J. EMBO*, 4:3831, 1985.
Song et al., Proc Natl Acad Sci USA, 103(11): p. 4305-10, 2006.
Sonnhammer et al., *Proc Int Conf Intell Syst Mol Biol* 6:175-182, 1998.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, In: *Human Gene Transfer*, Cohen-Haguenauer and Boiron (Eds.), John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Swift et al., *Proc Natl Acad Sci USA*, 109(10):p. 3997-4001, 2012.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
Thiesen et al., *J. Virology*, 62:614, 1988.
Top et al., *J. Infect. Dis.*, 124:155-160, 1971.
Trapnell et al., *Bioinformatics* 25:1105-1111, 2009.
Trapnell et al., *Nat Protoc* 7:562-578, 2012.
Tronche et al., *Mol. Biol. Med.*, 7:173, 1990.
Trudel and Constantini, *Genes and Dev.* 6:954, 1987.
Tupling et al., *Am J Physiol Cell Physiol* 301:C841-849, 2011.
Tur-Kaspa et al., *Mol. Cell Biol.*, 6:716-718, 1986.
Tyndell et al., *Nuc. Acids. Res.*, 9:6231, 1981.
Vannice and Levinson, *J. Virology*, 62:1305, 1988.
Varmus et al., *Cell*, 25:23-36, 1981.
Vasseur et al., *Proc Natl. Acad. Sci. U.S.A.*, 77:1068, 1980.
Wagner et al., *Proc. Natl. Acad. Sci. USA*, 87(9):3410-3414, 1990.
Wang and Calame, *Cell*, 47:241, 1986.
Wang et al., *Zhonghua Zhong Liu Za Zhi.*, 32:676-80, 2010.
Weber et al., *Cell*, 36:983, 1984.
Weinberger et al. *Mol. Cell. Biol.*, 8:988, 1984.
Wey and Goronzy, *Ann. NY Acad. Sci.*, 987:140-9, 2003.
Whitehead et al., Clin Exp Pharmacol Physiol, 33(7): p. 657-62, 2006.
Winoto and Baltimore, *Cell*, 59:649, 1989.
Wong et al., *Br J Cancer.*, 108:755-61, 2013.
Wong et A, *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Wu, *Cell Stem Cell*, 3:1-2, 2008.
Xie et al., *Nucleic Acids Res* 42:D98-103, 2014.
Yamauchi-Takihara et al., *Proc. Natl. Acad. Sci. USA*, 86(10):3504-3508, 1989.
Yang et al., *Proc. Natl. Acad. Sci. USA*, 87:9568-9572, 1990.
Yutzey et al., *Mol. Cell. Biol.*, 9:1397, 1989.
Zelenin et al., *FEBS Lett.*, 280:94-96, 1991.

What is claimed is:

1. A polynucleotide encoding a human Dwarf open reading frame (DWORF) polypeptide consisting of the sequence of SEQ ID NO: 3, wherein the polynucleotide has at least 80% identity to SEQ ID NO: 4, and is operatively linked to a heterologous muscle-specific or cardiac-specific promoter.

2. The polynucleotide of claim 1, wherein the polynucleotide has at least 85%, 90% or 95% identity to SEQ ID NO: 4.

3. The polynucleotide of claim 1, wherein the promoter is a muscle-specific promoter.

4. The polynucleotide of claim 1, wherein the promoter is a cardiac-specific promoter.

5. The polynucleotide of claim 4, wherein the cardiac-specific promoter is a cardiomyocyte-specific α-myosin heavy chain (αMHC) promoter.

6. The polynucleotide of claim 1, wherein the polynucleotide comprises SEQ ID NO: 4.

7. The polynucleotide of claim 1, wherein the polynucleotide is in a viral expression construct.

8. A vector, comprising a polynucleotide sequence encoding a human Dwarf open reading frame (DWORF) polypeptide consisting of the sequence of SEQ ID NO: 3, wherein the polynucleotide sequence has at least 80% identity to SEQ ID NO: 4, and is operatively linked to a heterologous muscle-specific or cardiac-specific promoter.

9. The vector of claim 8, wherein the polynucleotide sequence has at least 85%, 90% or 95% identity to SEQ ID NO: 4.

10. The vector of claim 9, wherein the vector is a viral vector.

11. The vector of claim 8, wherein the polynucleotide sequence comprises SEQ ID NO: 4.

12. The vector of claim 11, wherein the vector is a viral vector.

13. The vector of claim 8, wherein the vector is a viral vector.

14. The vector of claim 8, wherein the promoter is a muscle-specific promoter.

15. The vector of claim 8, wherein the promoter is a cardiac-specific promoter.

16. The vector of claim 15, wherein the cardiac-specific promoter is a cardiomyocyte-specific α-myosin heavy chain (αMHC) promoter.

17. A method of promoting the activity of the SERCA calcium pump in a subject suffering from dilated cardiomyopathy, comprising administering to the subject a viral particle comprising the polynucleotide of claim 1.

18. The method of claim 17, wherein the polynucleotide has at least 85%, 90% or 95% identity to SEQ ID NO: 4.

19. The method of claim 17, wherein the polynucleotide comprises SEQ ID NO: 4.

20. The method of claim 17, wherein the promoter is a cardiomyocyte-specific α-myosin heavy chain (αMHC) promoter.

* * * * *

SEQUENCE LISTING

<160> NUMBER OF SEQ ID NOS: 39

<210> SEQ ID NO 1
<211> LENGTH: 34
<212> TYPE: PRT
<213> ORGANISM: Mus

<400> SEQUENCE: 1

```
Met Ala Glu Lys Glu Ser Thr Ser Pro His Leu Met Val Pro Ile Leu
1               5                   10                  15

Leu Leu Val Gly Trp Ile Val Gly Cys Ile Ile Val Ile Tyr Ile Val
            20                  25                  30

Phe Phe
```

<210> SEQ ID NO 2
<211> LENGTH: 105
<212> TYPE: DNA
<213> ORGANISM: Mus

<400> SEQUENCE: 2

```
atggctgaga aagagtcaac atcaccacac ctcatggttc ccattcttct cctggttgga      60
tggattgtag gctgcatcat cgttatttac attgtcttct tctaa                    105
```

<210> SEQ ID NO 3

```
<211> LENGTH: 35
<212> TYPE: PRT
<213> ORGANISM: Homo sapiens

<400> SEQUENCE: 3

Met Ala Glu Lys Ala Gly Ser Thr Phe Ser His Leu Leu Val Pro Ile
1               5                   10                  15

Leu Leu Leu Ile Gly Trp Ile Val Gly Cys Ile Ile Met Ile Tyr Val
                20                  25                  30

Val Phe Ser
        35

<210> SEQ ID NO 4
<211> LENGTH: 108
<212> TYPE: DNA
<213> ORGANISM: Homo sapiens

<400> SEQUENCE: 4
atggctgaaa aagcggggtc tacattttca caccttctgg ttcctattct tctcctgatt     60
ggctggattg tgggctgcat cataatgatt tatgttgtct tctcttag                108

<210> SEQ ID NO 5
<211> LENGTH: 35
<212> TYPE: PRT
<213> ORGANISM: Artificial sequence
<220> FEATURE:
<223> OTHER INFORMATION: Synthetic peptide

<400> SEQUENCE: 5

Met Ala Glu Lys Ala Glu Ser Thr Ser Pro His Leu Met Val Pro Ile
1               5                   10                  15

Leu Leu Leu Val Gly Trp Ile Val Gly Cys Ile Ile Val Ile Tyr Ile
                20                  25                  30

Val Phe Phe
        35

<210> SEQ ID NO 6
<211> LENGTH: 108
<212> TYPE: DNA
<213> ORGANISM: Artificial sequence
<220> FEATURE:
<223> OTHER INFORMATION: Synthetic oligonucleotide

<400> SEQUENCE: 6
atggctgaga aagcagagtc aacatcacca caccctcatgg ttcccattct tctcctggtt    60
ggatggattg taggctgcat catcgttatt tacattgtct tcttctaa                 108

<210> SEQ ID NO 7
<211> LENGTH: 34
<212> TYPE: PRT
<213> ORGANISM: Artificial sequence
<220> FEATURE:
<223> OTHER INFORMATION: Synthetic peptide

<400> SEQUENCE: 7

Met Ala Glu Lys Glu Ser Thr Ser Pro His Leu Ile Val Pro Ile Leu
1               5                   10                  15

Leu Leu Val Gly Trp Ile Val Gly Cys Ile Ile Val Ile Tyr Ile Val
                20                  25                  30

Phe Phe
```

```
<210> SEQ ID NO 8
<211> LENGTH: 105
<212> TYPE: DNA
<213> ORGANISM: Artificial sequence
<220> FEATURE:
<223> OTHER INFORMATION: Synthetic oligonucleotide

<400> SEQUENCE: 8
atggctgaga aagagtcaac atcaccacac ctcattgttc ccattcttct cctggttgga      60
tggattgtag gctgcatcat cgttatttac attgtcttct ctaa                      105

<210> SEQ ID NO 9
<211> LENGTH: 35
<212> TYPE: PRT
<213> ORGANISM: Artificial sequence
<220> FEATURE:
<223> OTHER INFORMATION: Synthetic peptide

<400> SEQUENCE: 9

Met Ala Glu Lys Ala Glu Ser Thr Ser Pro His Leu Ile Val Pro Ile
1               5                   10                  15

Leu Leu Leu Val Gly Trp Ile Val Gly Cys Ile Ile Val Ile Tyr Ile
            20                  25                  30

Val Phe Phe
        35

<210> SEQ ID NO 10
<211> LENGTH: 108
<212> TYPE: DNA
<213> ORGANISM: Artificial sequence
<220> FEATURE:
<223> OTHER INFORMATION: Synthetic oligonucleotide

<400> SEQUENCE: 10
atggctgaga aagcagagtc aacatcacca cacctcattg ttcccattct tctcctggtt      60
ggatggattg taggctgcat catcgttatt tacattgtct cttctaa                   108

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ttcttctcct ggttggatgg                                                  20

<210> SEQ ID NO 12
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 12
tcttctaaat ggtgtcagat tgaagt                                           26

<210> SEQ ID NO 13
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 13
```

-continued tttacattgt cttcttctag aaaaggaaga ag    32

<210> SEQ ID NO 14
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 14
ccacccacca acaggaata    19

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
ttatgatgca gcccacaatc    20

<210> SEQ ID NO 16
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 16
tttccaaaag ataggaaata ctacagc    27

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
actcctggcc ctgactaagc    20

<210> SEQ ID NO 18
<211> LENGTH: 13
<212> TYPE: PRT
<213> ORGANISM: Artificial sequence
<220> FEATURE:
<223> OTHER INFORMATION: Synthetic peptide

<400> SEQUENCE: 18

Met Ala Glu Lys Glu Ser Thr Ser Pro His Leu Ile Cys
1               5                   10

<210> SEQ ID NO 19
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 19
tcattgcttc taagcagagt caaca    25

<210> SEQ ID NO 20
<211> LENGTH: 22

```
<212> TYPE: DNA
<213> ORGANISM: Artificial sequence
<220> FEATURE:
<223> OTHER INFORMATION: Synthetic oligonucleotide

<400> SEQUENCE: 20
atgcagccta caatccatcc aa                                              22

<210> SEQ ID NO 21
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 21
ccaggagaag aatg                                                       14

<210> SEQ ID NO 22
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 22
caggagacaa gaatg                                                      15

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
gtctgactag gtgtccttct                                                 20

<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 24
cgtcctcctg ctggtatag                                                  19

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ttacgtccat cgtggacagc                                                 20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
```
tgggctgggt gttagcctta        20

```
<210> SEQ ID NO 27
<211> LENGTH: 34
<212> TYPE: PRT
<213> ORGANISM: Mus

<400> SEQUENCE: 27
```

Met Ala Glu Lys Glu Ser Thr Ser Pro His Leu Ile Val Pro Ile Leu
1               5                   10                  15

Leu Leu Val Gly Trp Ile Val Gly Cys Ile Ile Val Ile Tyr Ile Val
            20                  25                  30

Phe Phe

```
<210> SEQ ID NO 28
<211> LENGTH: 34
<212> TYPE: PRT
<213> ORGANISM: Rattus

<400> SEQUENCE: 28
```

Met Ala Glu Lys Glu Ser Ala Ser Pro Gln Leu Met Val Pro Ile Leu
1               5                   10                  15

Leu Leu Val Gly Trp Ile Val Gly Cys Ile Ile Val Val Tyr Ile Val
            20                  25                  30

Phe Phe

```
<210> SEQ ID NO 29
<211> LENGTH: 34
<212> TYPE: PRT
<213> ORGANISM: Homo sapiens

<400> SEQUENCE: 29
```

Met Ala Glu Lys Gly Ser Thr Phe Ser His Leu Leu Val Pro Ile Leu
1               5                   10                  15

Leu Leu Ile Gly Trp Ile Val Gly Cys Ile Ile Met Ile Tyr Val Val
            20                  25                  30

Phe Ser

```
<210> SEQ ID NO 30
<211> LENGTH: 34
<212> TYPE: PRT
<213> ORGANISM: Rhesus

<400> SEQUENCE: 30
```

Met Ala Glu Lys Gly Ser Thr Phe Ser His Leu Leu Val Pro Ile Leu
1               5                   10                  15

Leu Leu Ile Gly Trp Ile Val Gly Cys Ile Ile Met Ile Tyr Val Val
            20                  25                  30

Phe Ser

```
<210> SEQ ID NO 31
<211> LENGTH: 34
<212> TYPE: PRT
<213> ORGANISM: Felis catus

<400> SEQUENCE: 31
```

Met Ala Glu Lys Glu Ser Thr Leu Ser His Leu Leu Val Pro Ile Leu
1               5                   10                  15

Leu Leu Ile Gly Trp Ile Val Gly Cys Ile Ile Met Val Tyr Val Val
            20                  25                  30

Phe Ser

<210> SEQ ID NO 32
<211> LENGTH: 34
<212> TYPE: PRT
<213> ORGANISM: Tenrec

<400> SEQUENCE: 32

Met Ala Glu Lys Glu Leu Val Ser Thr Arg Leu Leu Val Pro Leu Leu
1               5                   10                  15

Leu Phe Ile Gly Trp Ile Val Gly Cys Val Ile Met Ile Tyr Val Val
            20                  25                  30

Phe Ser

<210> SEQ ID NO 33
<211> LENGTH: 37
<212> TYPE: PRT
<213> ORGANISM: Lamprey

<400> SEQUENCE: 33

Met Glu Ala Thr Gly Leu Lys Lys Tyr Gln Arg Tyr Ala Val Pro Ala
1               5                   10                  15

Leu Leu Leu Leu Gly Trp Val Val Gly Cys Gly Leu Leu Thr Tyr Tyr
            20                  25                  30

Ser Leu Phe Arg His
            35

<210> SEQ ID NO 34
<211> LENGTH: 35
<212> TYPE: PRT
<213> ORGANISM: Xenopus

<400> SEQUENCE: 34

Met Glu Glu Thr Gly Ile Met Ala Tyr Lys Lys Phe Leu Val Pro Val
1               5                   10                  15

Leu Leu Gly Val Gly Trp Ile Ala Gly Cys Val Leu Met Ile Tyr Val
            20                  25                  30

Val Phe Ser
        35

<210> SEQ ID NO 35
<211> LENGTH: 35
<212> TYPE: PRT
<213> ORGANISM: Anolis

<400> SEQUENCE: 35

Met Ala Gln Thr Val Thr Val Pro Tyr Ser Gln Tyr Leu Val Pro Leu
1               5                   10                  15

Leu Leu Leu Ile Ala Trp Ile Val Gly Cys Val Leu Thr Val Tyr Phe
            20                  25                  30

Val Phe Ser
        35

<210> SEQ ID NO 36
<211> LENGTH: 25
<212> TYPE: DNA
<213> ORGANISM: Mus

<400> SEQUENCE: 36
gttcccattc ttctcctggt tggat                                                    25

```
<210> SEQ ID NO 37
<211> LENGTH: 27
<212> TYPE: DNA
<213> ORGANISM: Mus

<400> SEQUENCE: 37
gttcccattc ttgtctcctg gttggat                                            27

<210> SEQ ID NO 38
<211> LENGTH: 23
<212> TYPE: PRT
<213> ORGANISM: Mus

<400> SEQUENCE: 38

Met Ala Glu Lys Glu Ser Thr Ser Pro His Leu Met Val Pro Ile Leu
1               5                   10                  15

Val Ser Trp Leu Asp Gly Leu
            20

<210> SEQ ID NO 39
<211> LENGTH: 294
<212> TYPE: DNA
<213> ORGANISM: Mus

<400> SEQUENCE: 39
gaaagactcc tggccctgac taagccaccc aacaatagaa ataatggctg agaaagagtc        60
aacatcacca cacctcatgg ttcccattct tctcctggtt ggatggattg taggctgcat       120
catcgttatt tacattgtct tcttctaaaa aaggaagaag acttcaatct gacaccattt       180
agaagaataa aaatacagga atataactga ttattaaagg tgtcttgtat taaatagctg       240
tagtatttcc tatctttttgg aaactacaat tttttacatg agaatacatt aaga            294
```